United States Patent
Almås

(10) Patent No.: US 11,452,741 B2
(45) Date of Patent: *Sep. 27, 2022

(54) COMPOSITIONS AND METHODS FOR TREATING TRANSIENT BIOFILMS

(71) Applicant: WIAB WATER INNOVATION AB, Malmo (SE)

(72) Inventor: Geir Hermod Almås, Snarøya (NO)

(73) Assignee: WIAB WATER INNOVATION AB, Malmo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/672,395

(22) Filed: Nov. 1, 2019

(65) Prior Publication Data
US 2020/0061107 A1 Feb. 27, 2020

Related U.S. Application Data

(63) Continuation-in-part of application No. 15/852,622, filed on Dec. 22, 2017, which is a continuation-in-part of application No. 15/612,571, filed on Jun. 2, 2017, which is a continuation-in-part of application No. 15/267,220, filed on Sep. 16, 2016, which is a continuation of application No. 15/167,076, filed on May 27, 2016, now Pat. No. 10,675,299, which is a continuation-in-part of application No. 14/618,820, filed on Feb. 10, 2015, and a continuation-in-part of application No. 14/618,799, filed on Feb. 10, 2015, now Pat. No. 10,577,244, application No. 14/618,820, which is a continuation-in-part of application No. 13/770,738, filed on Feb. 19, 2013, now Pat. No. 9,492,479, application No. 14/618,799, which is a continuation-in-part of application No. 13/770,738, filed on Feb. 19, 2013, now Pat. No. 9,492,479.

(60) Provisional application No. 62/755,113, filed on Nov. 2, 2018, provisional application No. 62/438,189, filed on Dec. 22, 2016, provisional application No. 62/438,204, filed on Dec. 22, 2016, provisional application No. 62/438,198, filed on Dec. 22, 2016, provisional application No. 62/438,202, filed on Dec. 22, 2016, provisional application No. 61/600,344, filed on Feb. 17, 2012.

(51) Int. Cl.
| | |
|---|---|
| *A61K 33/20* | (2006.01) |
| *C01B 11/04* | (2006.01) |
| *A61K 31/19* | (2006.01) |
| *A61K 9/00* | (2006.01) |

(52) U.S. Cl.
CPC ............ *A61K 33/20* (2013.01); *A61K 9/0014* (2013.01); *A61K 31/19* (2013.01); *C01B 11/04* (2013.01)

(58) Field of Classification Search
CPC ...... A61K 33/20; A61K 9/0014; A61K 31/19; C01B 11/04
See application file for complete search history.

(56) References Cited

U.S. PATENT DOCUMENTS

| | | | |
|---|---|---|---|
| 2,438,781 | A | 3/1948 | Kamlet |
| 4,017,592 | A | 4/1977 | Penard et al. |
| 4,713,251 | A | 12/1987 | Seighman |
| 4,983,634 | A | 1/1991 | Corby |
| 5,152,915 | A | 10/1992 | Ralston, Jr. et al. |
| 5,456,211 | A | 10/1995 | Stevenson |
| 6,333,054 | B1 | 12/2001 | Rogozinski |
| 6,564,508 | B1 | 5/2003 | Buchan |
| 6,627,207 | B1 | 9/2003 | Petersen |
| 6,764,693 | B1 | 7/2004 | Smith |
| 8,449,916 | B1 | 5/2013 | Bellaire et al. |
| 8,784,900 | B2 | 7/2014 | Northey |
| 10,029,917 | B2 | 7/2018 | Almas et al. |
| 2006/0014017 | A1 | 1/2006 | Pilotek et al. |
| 2008/0008621 | A1 | 1/2008 | Ikeda et al. |
| 2009/0247485 | A1 | 10/2009 | Ahmed et al. |
| 2009/0258083 | A1 | 10/2009 | Calderon |
| 2010/0112092 | A1 | 5/2010 | Northey |
| 2012/0148516 | A1 | 6/2012 | Abel et al. |
| 2012/0164235 | A1 | 6/2012 | Northey |
| 2013/0215709 | A1 | 8/2013 | Hinderson |
| 2013/0216628 | A1 | 8/2013 | Hinderson et al. |
| 2015/0150906 | A1 | 6/2015 | Hinderson et al. |
| 2015/0150907 | A1 | 6/2015 | Hinderson et al. |

(Continued)

FOREIGN PATENT DOCUMENTS

| | | |
|---|---|---|
| EP | 1829449 A1 | 9/2007 |
| EP | 2937101 A1 | 10/2015 |

(Continued)

OTHER PUBLICATIONS

International Search Report and Written Opinion dated Jul. 30, 2013, for International Application No. PCT/IB2013/000682, filed Feb. 19, 2013 (7 pages).

(Continued)

*Primary Examiner* — Robert S Cabral
(74) *Attorney, Agent, or Firm* — Brown Rudnick LLP; Thomas C. Meyers

(57) ABSTRACT

Disinfecting compositions containing hypochlorous acid and acetic acid are useful for treating transient biofilms in or on tissue without harming the natural flora of the tissue. The compositions are useful for treating a variety of types of tissue. Compositions are useful for treating and preventing orally-associated biofilm. Compositions may be provided in mouthwash form, spray form, gel form, cream form, dentifrice form, and may include nanoparticle encapsulated molecules for controlled release.

6 Claims, 18 Drawing Sheets

(56) References Cited

U.S. PATENT DOCUMENTS

| | | |
|---|---|---|
| 2015/0231173 A1 | 8/2015 | Sampson et al. |
| 2015/0264935 A1 | 9/2015 | Chang |
| 2016/0271171 A1 | 9/2016 | Almas |
| 2017/0266227 A1 | 9/2017 | Almas |

FOREIGN PATENT DOCUMENTS

| | | |
|---|---|---|
| JP | H10309582 A | 11/1998 |
| JP | 2003040716 A | 2/2003 |
| JP | 2003-511473 A | 3/2003 |
| JP | 2007-326050 A | 12/2007 |
| JP | 2009274950 A | 11/2009 |
| JP | 2011056377 A | 3/2011 |
| JP | 2011-229833 A | 11/2011 |
| JP | 2013/515021 A | 5/2013 |
| WO | 1994021125 A1 | 9/1994 |
| WO | 2001028336 A1 | 4/2001 |
| WO | 2005065383 A2 | 7/2005 |
| WO | 2006/057311 A1 | 6/2006 |
| WO | 2011014809 A1 | 2/2011 |
| WO | 2012123695 A2 | 9/2012 |
| WO | 2013121294 A1 | 8/2013 |
| WO | 2015/082937 A2 | 6/2015 |
| WO | 2017203364 A1 | 11/2017 |

OTHER PUBLICATIONS

Kuroiwa, K., et al., "Augmenting effect of acetic acid for acidification on bactericidal activity of hypochlorite solution", Lett. Applied Microbiol., 2003, pp. 46-49 (4 Pages).

Wang, L., et al., "Hypoohlorous Acid as a Potential Wound Care Agent", J Burns Wounds, 2007, pp. 65-79 (15 Pages).

Dash, Sukalyan et al. "Oxidation by Permanganate: Synthetic and Mechanistic Aspects," Tetrahedron, vol. 65, 2009, pp. 707-739 (33 Pages).

Boddie, R.L. et al., "Efficacy of Teat Dips Containing a Hypochlorous Acid Germicide Against Experimental Challenge with *Staphylococcus aureus* and *Streptococcus agalactiae*", J. Dairy Sci., 1996, pp. 1683-1688 (6 Pages).

Schmittinger, P. et al. "Chlorine", Wiley, 2000, pp. 160-164 (7 Pages).

Plaizier-Vercammen, Jacqueline, "Rheological Properties of Laponite XLG, A Synthetic Purified Hectorite", Die Pharmazie: An International Journal of Pharmaceutical Sciences, Govi Verlag Pharmazeutischer Verlag GMBH, DE, vol. 47, No. 11, Nov. 1992, pp. 856-861 (6 Pages).

International Search Report and Written Opinion of the International Searching Authority dated Sep. 8, 2017 for International Application No. PCT/IB2017/000757 (17 Pages).

Puttaiah, R., et al., "Dental Unit Water Line Treatment with Sodium Hypochlorite and Acetic Acid", Michochemical Journal, 1998, pp. 333-340 (8 Pages).

International Search Report and Written Opinion of the International Searching Authority dated May 17, 2018 for International Application No. PCT/IB2017/001728 (17 Pages).

Dasgupta et al., Mol. Pharmaceutics 12:3479-3489.

Feng et al. 2007, J. Environ. Eng. Sci. 6, 277-284.

Gao, et al. The Journal of Antibiotics, (2011) 64, 625-634.

Grijalvo, et al., The Royal Socitey of Chemistry, Biomater. Sci., 2016, 4, 555-574.

Lee et al., Dovepress, International Journal of Nanomedicine, 2016:11 285-297.

Tzanavaras et al., 2007 Central European Journal of Chemistry, pp. 1-12.

Weiniger et al, 2012 Anaesthesia, 67, 906-916.

Binnebose, et al., 2015 Journal PLOS Neglected Tropical Disease, DOI:10. 1371, pp. 1-18.

Campos, et al., Scientific Reports, pp. 1-14.

Pandey, et al., 2013, Biodegradeable Polymers for Potential Delivery Systems for Therapeutics, Multifaceted Development and Application of Polymers for Biology, Biomedicine and Nanotechnology. Springer, Berlin, Heidelberg, 169-202.

Akbarzadeh et al, "Liposome: classification, preparation, and application," Nanoscale Res Lett, 2013, 8:102, 9 pages.

Borkow et al, "Copper, An Ancient Remedy Returning to Fight Microbial, Fungal and Viral Infections," Current Chemical Biology, 2009, 3, pp. 272-278.

Chinese Office Action and the English translation issued in Chinese Application No. 2017800868745, dated Oct. 21, 2020, 14 pages.

English translation of the Office Action issued in Eurasian Patent Application No. 201892805, dated Feb. 19, 2020, 3 pages.

Exam Report issued in Indian Application No. 201817044946, dated Jul. 6, 2020, 17 pages.

Exam Report issued in Phillippines Application No. 1-2018-502506, dated Oct. 28, 2020, 4 pages.

Grijaivo et al, "Biodegradable liposome-encapsulated hydrogels for biomedical applications: A marriage of convenience," Biomaterials science 4.4, 2016, pp. 555-574.

Henry, "Experiments on the Quantity of Gases absorbed by Water, at different Temperatures, under different Pressures," downloaded from rstl.royalsocietypublishing.org on Jan. 4, 2010, 18 pages.

Mozafari, "Nanoliposomes: Preparation and Analysis," Liposome, Methods in Molecular Biology, vol. 605, pp. 29-50.

Non-Final Office Action issued in U.S. Appl. No. 15/267,220, dated Sep. 18, 2020, 56 pages.

Non-Final Office Action issued in U.S. Appl. No. 15/852,615, dated Oct. 19, 2020, 17 pages.

Romling et al., Biofilm infections, their resilience to therapy and innovative treatment strategies, Journal of Internal medicine, 272.3, 2012, 541-561.

Setlow, "Spores of Bacillus subtilis: their resistance to and killing by radiation, heat and chemicals," Journal of Applied Microbiology 101, 2006, pp. 514-525.

Chinese Office Action issued in Chinese Application No. 201780042967.8, dated Jun. 2, 2021, 18 pages.

European Office Action issued in European Patent Application No. 17847767.5, dated Apr. 19, 2021, 4 pages.

European Office Action issued in European Patent Application No. 17847769.1, dated Apr. 30, 2021, 9 pages.

Indonesian Exam report issued in Indonesia Patent Application No. PID201905970, dated Aug. 26, 2021, 3 pages.

Japanese Office Action and English translation issued in Japanese Application No. 2019-514872, dated Apr. 15, 2021, English translation obtained from google translate which can be accessed at https://translate.google.com, 5 pages.

Japanese Office Action issued in Japanese Application No. 2019-534688, dated Oct. 12, 2021, 7 pages.

Korean Preliminary Rejection issued in Korean Patent Application No. 10-2018-7037219, dated Jul. 2021, 4 pages.

Non-Final Office Action issued in U.S. Appl. No. 15/852,767, dated May 26, 2021, 13 pages.

Notice of Decision issued in Saudia Arabian Application No. 518400529, dated Jun. 8, 2021, 2 pages.

Notice of Decision issued in Saudia Arabian Application No. 519402147, dated Jan. 17, 2022, 2 pages.

Office Action issued in Philippines Patent Application No. 1-2018-502506, dated Jun. 9, 2021, 3 pages.

Park, 2005, Effects of silver nanoparticles on the fluidit of bilayer in phospholipid liposome, Colloids and Surfaces B: Biointerfaces 44.2-3:117-122.

Subsequent Substantive Examination Report issued in Philippines Application No. 1-2018-502506, dated May 25, 2021, 4 pages.

24 hours filter-grown P. aeruginosa biofilms

Log10 reduction cfu/ml

After 2 h treatment

| HAc / HOCl | 0 ppm | 50 ppm | 100 ppm | 150 ppm | 200 ppm |
|---|---|---|---|---|---|
| 0.25% | | | 0.00 | 5.57 | 8.75 |
| 0.5% | 0.18 | 0.35 | 0.92 | 5.24 | 8.75 |
| 1% | 0.00 | 0.00 | 1.11 | 3.77 | 4.00/8.75 |
| 1.5% | 0.19 | 0.00 | 1.13 | | 8.75 |
| 2% | | | 1.42 | | 8.75 |

After 2+2 h treatment

| HAc / HOCl | 0 ppm | 50 ppm | 100 ppm | 150 ppm | 200 ppm |
|---|---|---|---|---|---|
| 0.25% | | | 3.00 | 8.66 | 8.75 |
| 0.5% | 0.15 | 1.86 | 7.31 | 8.66 | 8.75 |
| 1% | 0.00 | 1.08 | 8.65 | 8.80 | 8.80 |
| 1.5% | 0.00 | 1.23 | 8.65 | | 8.75 |
| 2% | | | 8.65 | | 8.75 |

FIG. 19

COMPOSITIONS AND METHODS FOR TREATING TRANSIENT BIOFILMS

RELATED APPLICATIONS

This application is a continuation-in-part of U.S. patent application Ser. No. 15/852,622, filed Dec. 22, 2017, which claims priority to and the benefit of U.S. Provisional Patent Application Ser. No. 62/438,189, filed Dec. 22, 2016, U.S. Provisional Patent Application Ser. No. 62/438,198, filed Dec. 22, 2016, U.S. Provisional Patent Application Ser. No. 62/438,202, filed Dec. 22, 2016, and U.S. Provisional Patent Application Ser. No. 62/438,204, filed Dec. 22, 2016; and is a continuation-in-part of U.S. patent application Ser. No. 15/612,571, filed Jun. 2, 2017.

Additionally, U.S. patent application Ser. No. 15/612,571 claims priority to and the benefit of U.S. Provisional Patent Application Ser. No. 62/438,198, filed Dec. 22, 2016, and U.S. Provisional Patent Application Ser. No. 62/438,204, filed Dec. 22, 2016; and is a continuation-in-part of U.S. patent application Ser. No. 15/267,220, filed Sep. 16, 2016, which is a continuation of U.S. patent application Ser. No. 15/167,076, filed May 26, 2016, which is: (1) a continuation-in-part of U.S. patent application Ser. No. 14/618,820, filed Feb. 10, 2015, which is a continuation-in-part of U.S. patent application Ser. No. 13/770,738, filed Feb. 19, 2013, which claims priority to and the benefit of U.S. Provisional application Ser. No. 61/600,344, filed Feb. 17, 2012; and (2) a continuation-in-part of U.S. patent application Ser. No. 14/618,799, filed Feb. 10, 2015, which is a continuation of U.S. patent application Ser. No. 13/770,738, filed Feb. 19, 2013, which claims priority to and the benefit of U.S. Provisional application Ser. No. 61/600,344, filed Feb. 17, 2012.

The contents of each of the above-referenced applications are incorporated by reference herein in their entirety.

FIELD OF THE INVENTION

The invention generally relates to compositions of acetic acid and hypochlorous acid for treating transient biofilm infection, while maintaining the natural flora. The invention relates to compositions of acetic acid and hypochlorous acid for the treatment of oral biofilm.

BACKGROUND

Healthcare professionals have been relying on the use of hand disinfectants as an alternative or supplement to handwashing for some time now because they are less abrasive and easier than washing with antimicrobial soap and water. And when the Food and Drug Administration published an article barring consumers from purchasing and using certain antibacterial soaps, the rise of the use of hand disinfectants spread amongst the broader population. Hand disinfectants or hand sanitizers are generally gel, foam, or liquid solutions with an active ingredient for killing microorganisms. Most hand disinfectants include alcohol in the form of ethanol or isopropanol.

It is readily known that alcoholic hand rubs significantly reduce the skin flora count immediately and up to three hours after disinfection. However, the skin flora not only consists of "bad" microbes, but also consists of microorganisms that are generally nonpathogenic or commensal, and are even beneficial to one's health. An example of such a microbe is *Staphylococcus epidermidis*. Much like the bacteria of the gut, the natural skin flora plays an active role in protecting the host. For example, resident skin flora inhibits the growth of transient bacteria and maintains the balance between the colonizing microorganisms. The natural skin microbiota plays an integral role in eliciting the host immune networks. (Br J Dermatol. 2008 March; 158(3): 442-455). As such, the significant reduction of resident skin flora for a prolonged period of time leaves the host defenseless against microbial infection.

When exposed to alcohol, *Staphylococcus aureus* and other transient bacteria that survive respond by producing a protective biofilm. When the natural skin microbes have been eradicated by alcohol, they are unable to protect against the colonization of such pathogenic microbes. Biofilms are known to impair cutaneous wound healing and reduce topical antibacterial efficiency, and they can also spread bacteria into the air. Microbial infections that produce biofilms can pose serious health problems. Scientists estimate that up to 80% of all infections affecting mammals are biofilm infections. Meanwhile, antibiotic resistant transient bacteria such as MRSA (methicillin-resistant *Staphylococcus aureus*) proliferate within the biofilm, leading to many serious and deadly infections. Dysbiosis of the natural skin microbiome predisposes the host not only to disease and infection, but also other inflammatory and immunological diseases. (Prescott et al. World Allergy Organization Journal (2017) 10:29).

Though, only a small number of transient bacteria cause biofilm infections, the presence of the natural microbes are important for fighting and protecting against those harmful transient microbes. There is a need for disinfectants that are not harmful to the natural microbes of the skin.

Prior art disinfectant compositions have various shortcomings. Some eradicate the natural flora while treating transient bacteria. Some have long recovery times, leaving the tissue defenseless against pathogenic bacterial infection. Others are unable to prevent pathogenic bacteria infection.

SUMMARY

Antimicrobial compositions comprising hypochlorous acid and an organic acid, such as acetic acid, as described herein are useful for treating transient microbes without harming natural microbial flora. For example, compositions comprising hypochlorous acid and acetic acid are useful for treating biofilms on skin while maintaining the homeostasis of the natural skin microbiota. Compositions of the invention are useful for disinfecting skin without negatively impacting the protective qualities of the bacteria that naturally exists on skin. Compositions of the invention are thus effective for hand disinfection. Compositions of hypochlorous acid and acetic acid are also effective for treatment of pathogenic transient microbes found in nasal passages, the vagina, and the oral cavity. Compositions of the invention reduce or eliminate pathogenic bacteria while maintaining homeostatis of the microbiota naturally present on skin. The concentrations of HOCl and HAc are balanced in order to achieve a synergistic effect, resulting in the antimicrobial capabilities of the composition being greater than would be expected based on the antimicrobial properties of each component on its own. Acetic acid provides an important buffering capacity that allows optimal performance of hypochlorous acid, especially in environments in which the tendency is to drive pH to homeostatic levels. For example, in the oral cavity the natural pH is about 7.4 and acetic acid provides a buffering capacity in that environment to allow optimal activity of HOCl. In addition, the hypochlorous acid modulates the toxicity of the acetic acid and provides an analgesic effect, allowing stronger compositions to be applied to skin or other tissue without adverse side effects, patient discomfort, or eradication of the natural flora. Finally, acetic acid is particularly effective against anaerobic bacteria, such as Pseudomona. In addition to acetic acid, other organic acids, such as ascorbic acid, lactic acid, formic acid, malic acid, citric acid, uric acid, and other carboxylic acids or sulfonic acids.

Various compositions are described herein, having different concentrations of each acid component for treatment of diverse types of tissues. Acetic acid concentrations from about 0.1% to about 5% are useful. Likewise, hypochlorous acid is found in different concentrations in the compositions depending on the type of tissue being treated. For example, hypochlorous acid at 80 to 2500 ppm is useful for treating a biofilm infecting the root of a tooth, while only 5-60 ppm is needed for a dental mouthwash composition, and between 30-100 ppm is to eliminate transient biofilm of skin, while maintaining the natural flora. In general, hypochlorous acid should be present in a concentration of up to about 2500 ppm. Compositions of the invention are particularly effective at biofilm reduction due to the synergistic balance between hypochlorous acid and acetic acid, which gives the compositions the dual effect of surface, just beneath surface, and deeper subsurface treatment of biofilm. In general, hypochlorous acid is able to act rapidly at or near the surface; whereas acetic acid takes longer time to act and therefore can act below the tissue surface.

The disclosed acetic acid and hypochlorous acid compositions are effective against transient microflora on tissue or non-tissue surfaces without affecting the natural biofilm. Application of the compositions to the skin aids in combating microbial infection by preventing and treating transient bacterial infections, including biofilms, while maintaining the natural microbiome of the skin. Compositions of the invention are useful for hand washing and disinfecting surface area. Compositions of the invention are useful for treating transient bacteria on epidermal tissue. The disclosed acetic acid and hypochlorous acid compositions are effective against treating transient bacteria on dermal tissue.

Compositions of the invention are also useful for treating orally-associated transient biofilm. Compositions of the invention are effective in treating transient biofilm on the teeth, gums, gingiva, tongue and oral mucosa. Application of the disclosed compositions of acetic acid and hypochlorous acid to the teeth or oral mucosa treats transient biofilm infection while not harming the natural flora of the mouth. The inventive compositions are effective in treating dental plaque, tooth hypersensitivity, and dental disease. Application of a prophylactically effective amount of the disclosed acetic acid and hypochrlous acid compositions aids in preventing orally-associate biofilm. Compositions of acetic acid and hypochlorous acid are effective in preventing dental plaque biofilm. Additionally, the disclosed compositions of acetic acid and hypochlorous acid are effective in sterilizing a root canal.

Compositions of the invention may be provided as a gel or cream, which allows longer contact time with the tissue. Additionally, one or both of the components of inventive compositions can be encapsulated in a nanoparticle for controlled or delayed release. The disclosed acetic acid and hypochlorous acid compositions may also be provided as a dentifrice or mouthwash.

The compositions described herein can be combined with various excipients and carriers to facilitate topical administration. Hypochlorous acid and acetic acid products can take the form of gels, creams, lotions, sprays, liquids, foams, powders, varnishes, paints, and other delivery formulations known in the art. Alternatively, the compositions provided can be incorporated into cloth or fibrous wipes, or applied to bandages, dressing, gauze, brushes, and implants and permitted to dry into a film.

The hypochlorous acid and acetic acid compositions described herein can also be combined with a fluoride-containing composition or a liquid polymer formulation. Application of compositions comprising acetic acid, hypochlorous acid and liquid polymer formulation to an oral surface helps to prevent transient biofilm infection. Compositions of the invention can be applied to adhesive strips. Application of the adhesive strips to the teeth or other oral surface is effective in treating and preventing transient biofilm infection.

In certain aspects, the invention includes a composition made up of acetic acid and hypochlorous acid. The acetic acid is present in concentrations greater than about 0.1%, and preferably less than about 5.0%. A preferred hypochlorous acid concentration is between about 5 ppm and about 2500 ppm. In various embodiments the particular concentrations of acetic acid and hypochlorous acid depend on the intended treatment area and how deep beneath the surface of the tissue the treatment is desired.

In some embodiments, acetic acid is present in a concentration sufficient to penetrate beneath the surface of a tissue. In some embodiments, acetic acid concentration is greater than about 0.12%, and preferably greater than about 0.2%, and in some embodiments it is about 0.5% or more. The acetic acid may be encapsulated in a nanoparticle for controlled or delayed release. In some embodiments, the hypochlorous acid is present in a concentration sufficient to treat biofilm on and just beneath a surface of tissue and not eradicate the natural flora. The composition may further include a gel, cream, ointment, oil, liquid polymer, or fluoride.

In related aspects, the invention involves methods for treating a transient biofilm in or on tissue without harming the natural flora of the tissue. Methods include applying to a tissue a composition comprising acetic acid in a concentration sufficient to penetrate tissue and hypochlorous acid in an amount sufficient to remove transient biofilm on and just beneath a surface of the tissue. Methods include applying to teeth or oral surface a composition comprising acetic acid and hypochlorous acid to treat orally-associated biofilm and not harming the natural flora. Methods include applying a composition comprising acetic acid in a concentration sufficient to prevent transient biofilm on oral mucosa and on teeth.

In some embodiments, the tissue to be treated is the epidermis and the hypochlorous acid concentration is about 10-200 ppm. In still other embodiments, the tissue to be treated is vaginal tissue, and the hypochlorous acid concentration is about 5-100 ppm, and the acetic acid concentration is between about 0.1% and about 5.0%.

The acetic acid may be present in amounts sufficient to remove transient biofilm beneath the surface of the oral mucosa or the tooth root. The acetic acid may be present in an amount from about 0.1% to about 2.0%, and the hypochlorous acid may be present in a concentration from about 5 ppm to about 250 ppm.

BRIEF DESCRIPTION OF THE DRAWINGS

FIGS. 15-21 provide data on the reduction of various biofilms when exposed to compositions of acetic acid and hypochlorous acid at different concentrations, compared with commercially available biofilm treatments.

DETAILED DESCRIPTION

Figure 1:
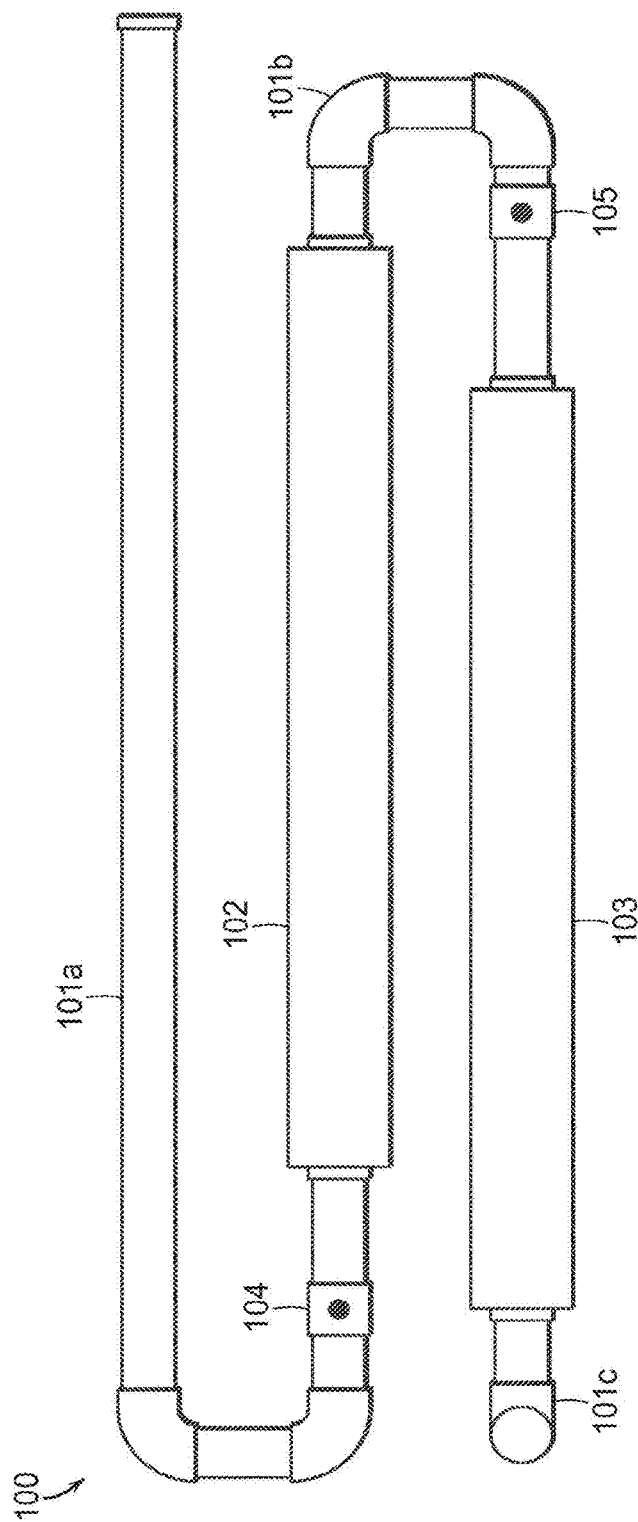
FIG. 1 is a schematic showing an exemplary system for producing hypochlorous acid according to methods of the invention.

Treatment of bacterial infection and biofilm is achieved using a synergistic composition comprising an organic acid, such as acetic acid, and hypochlorous acid. The acetic acid component is particularly effective for penetrating tissue, while the hypochlorous acid is particularly effective for treating biofilm on the outer surface of tissue. Acetic acid can penetrate up to 2 mm or more beneath the surface of a wound to treat otherwise difficult to reach biofilms.

Preferred compositions of the invention comprise hypochlorous acid in synergistic combination with acetic acid. It has been discovered that a balanced composition in which a biocidal amount of acetic acid (or an equivalent organic acid) optimized with hypochlorous acid achieves maximum therapeutic benefit, whether applied to a surface or in a manner designed to penetrate skin. For example, for surface applications, the relative amount of acetic acid to hypochlorous acid is lower than for penetrative applications. According to the invention, surface bacterial contamination or biofilm is sufficiently treated by hypochlorous acid with a lower amount of acetic acid; but for applications requiring deep penetration (e.g., wounds), the amount of acetic acid must be increased. In that case, hypochlorous acid is used to moderate the toxicity of the acetic acid to surrounding tissue, while allowing the acetic acid to attack the biofilm. In addition, it has been discovered that the synergistic combination of acetic acid and hypochlorous acid selectively kill harmful biofilm while preserving beneficial biofilm. Compositions of the invention comprise balanced concentrations of acetic acid and hypochlorous acid in order to selectively kill harmful biofilm. Concentrations are also balanced in consideration of the application to which they are directed (e.g., surface treatment of a tooth or skin versus deep tissue treatment of a wound or tooth root). The application provides guidance on the synergistic effects of various combinations of acetic acid and hypochlorous acid. The skilled artisan can determine, based upon the information provided in the instant specification, the relative amounts of acetic acid and hypochlorous acid necessary for treatment of any bacterial infection or biofilm formation.

Treating both the surface-level and subdermal infections provides a dual action treatment that is particularly needed for wound care. Chronic wounds and eczema are plagued by biofilm that affects subsurface parts of the wound. These wounds frequently have *S. aureus* infections which typically exist on or near the surface and prevent the wound from closing and healing. Also, *P. aeruginosa* infection is often present, which is generally deeper, underneath the surface of the wound. When a deep infection is present, it is important to keep the wound open and hydrated while healing from the inside out, to prevent the wound from closing before the deeper infection is healed. Only treating the surface-level infection causes the wound to close and trap the deeper biofilm inside the tissue, which can lead to sepsis and other complications.

Figure 22:
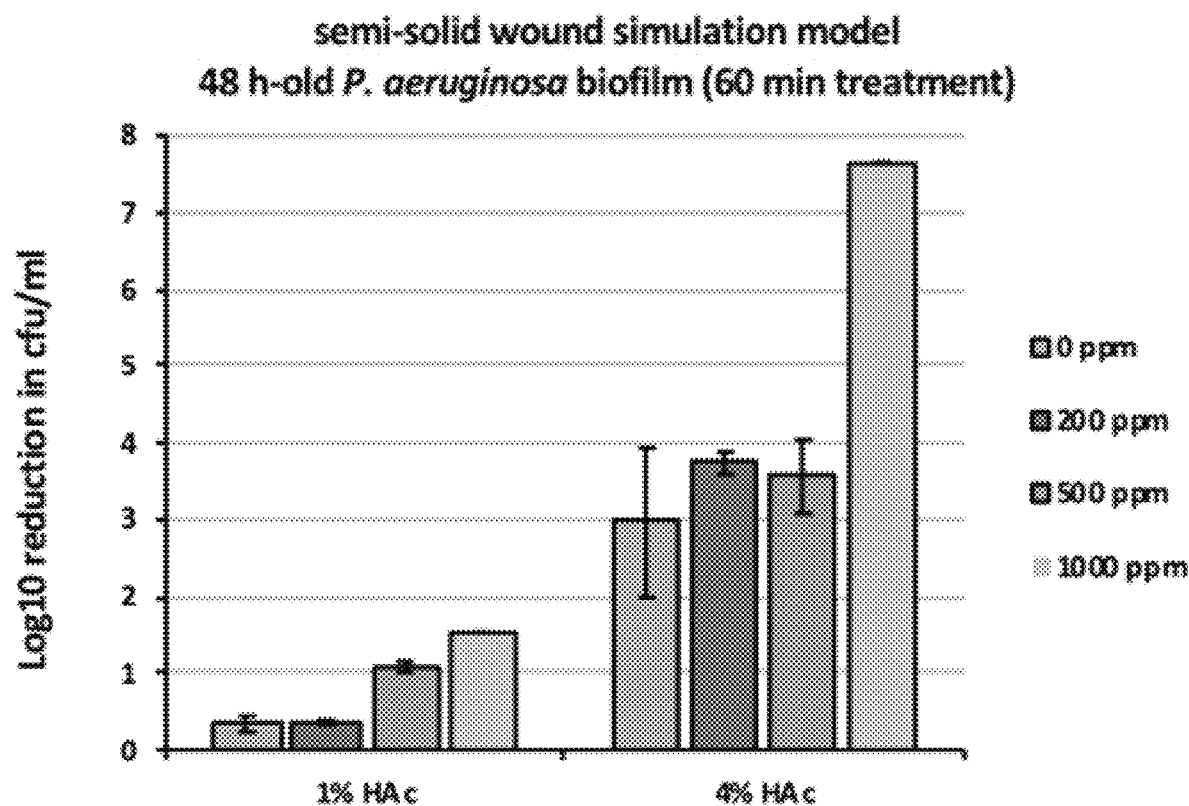
FIG. 22 is a graph showing the killing effect of various concentrations of HOCl with either 1% or 4% acetic acid.
Figure 23:
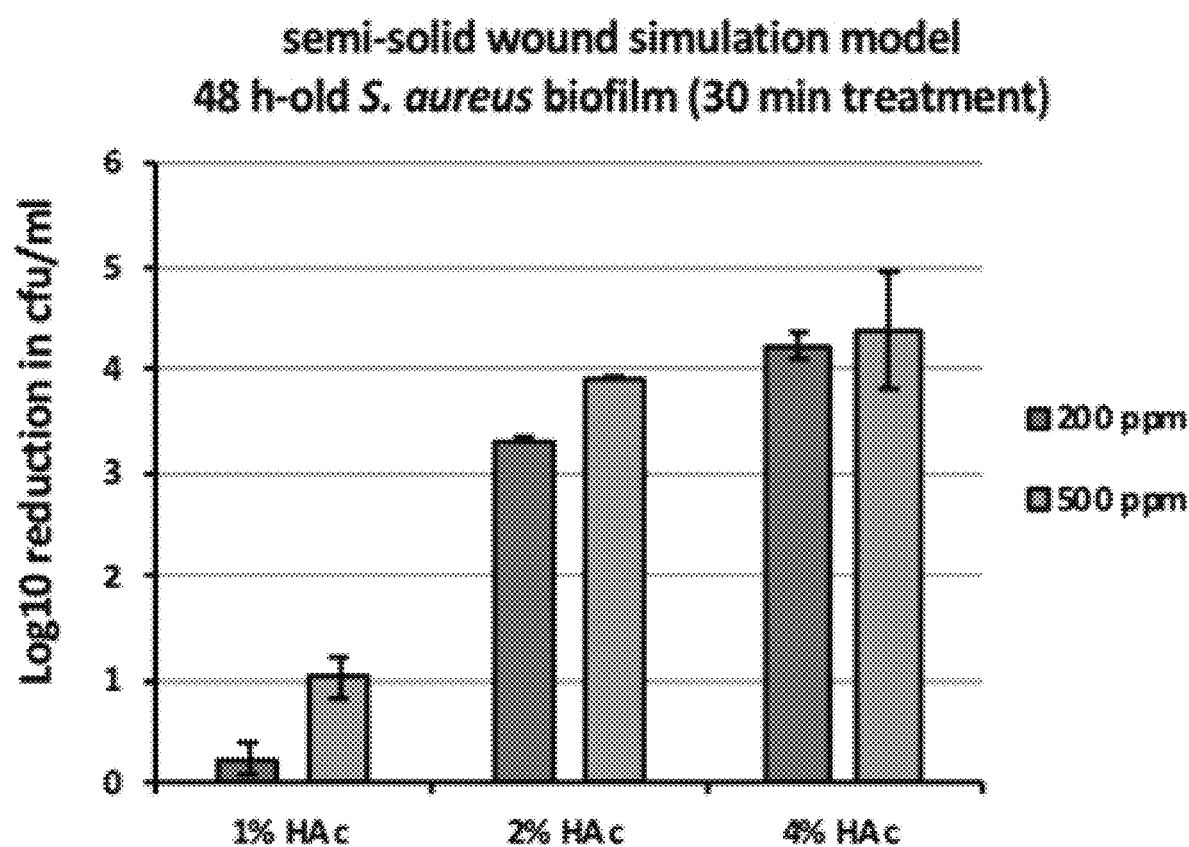
FIG. 23 is a graph showing the killing effect of HOCl at 200 ppm and 500 ppm with either 1%, 2% or 4% acetic acid.

A feature of the invention is also seen in the modulation of hypochlorous acid and acetic acid. For example, increasing the concentration of either HOCl or acetic acid, while holding the other constant, increases the bacterial killing effect of the combination. In addition, increasing the concentration of acetic acid increases the killing effect in a "dirty" sample, i.e., one that contains organics (such as blood, sputum and other organic compounds). Thus, in a dirty sample, the concentration of acetic acid is more important to modulate. FIG. 22 shows the killing effect of various concentrations of HOCl with either 1% or 4% acetic acid. FIG. 23 shows that the biggest jump in killing effect happens between 1% and 2% acetic acid. Both FIGS. 22 and 23 are the result of applying the various concentrations of HOCl and acetic acid to a wound simulation model of infection with *Pseudomonas aeruginosa*.

There are numerous applications of the invention to prevent and/or treat biofilm. For example, a frequent problem with diabetic foot ulcers, for example, is that they close at the surface, creating an open cavity beneath. The cavity will contain pus as part of the immune system response, which consists of debris, bacteria, and white blood cells. Pus contained in a closed compartment, particularly in a foot ulcer, can help spread the infection and potentially cause sepsis. In an open wound properly dressed, however, the pus will be discharged into the wound bed and the dressing. The bacteria that survive the pus environment inside a closed wound can spread infection. Therefore, removing the *S. aureus* infection without first or simultaneously removing the *P. aeruginosa* infection may not completely eradicate biofilm infection, leading to early closure and possibly sepsis.

Antimicrobial solutions, such as compositions provided herein, reduce infection in the deep areas of the wound bed and allow wound healing from the inside out, so that the surface does not heal faster than the inner wound. Acetic acid is present in an amount sufficient to disinfect a biofilm beneath the wound bed, and hypochlorous acid is present in an amount sufficient to disinfect the surface of the wound. The composition therefore allows complete disinfection of the wound to prevent premature closing and trapping a biofilm beneath the surface of a closed wound.

The disclosed compositions are particularly effective because balancing the concentrations of hypochlorous acid and acetic acid allows treatment of the surface level biofilm and also the subsurface biofilm. The precise balance depends on the treatment site and the amount of surface penetration that is desired. The hypochlorous acid can be present in about 10 ppm up to about 500 ppm or more. Different uses and types of tissue may require higher or lower concentrations. The acetic acid may be present at about 0.25% up to about 2.0% or more, and preferably about 1.0%. By balancing the two components, the composition can have the dual effect of treating at the surface and beneath the surface of the tissue or wound.

Compositions consistent with the present disclosure can be created for a variety of uses. For example, a composition of relatively low acetic acid (as low as about 0.05%) and about 5-60 ppm of hypochlorous acid is a useful composition as a mouthwash for combating infection in dental tissue. The lower concentration of acetic acid is sufficient in mouthwash compositions because the microbial infection does not tend to penetrate deep within the tissue.

For wound treatment, on the other hand, a composition may include a higher concentration of acetic acid (about 1.0%, about 2.0%, about 3.0%, about 4.0%, or about 5.0%) to more effectively treat the biofilm deep inside the tissue.

Other uses may require more or less of each component. For example, a composition with hypochlorous acid concentration of about 80-250 ppm is useful for flushing a bladder, a treatment that is often needed for patients with a urinary catheter to prevent infection or blockage. A composition having a hypochlorous acid concentration of about 15-60 ppm is sufficient for treatment of an infected lung.

In certain embodiments, the composition is in the form of a gel, which allows longer contact times with the wound. Rinsing with a solution may not be sufficient, as the contact time of the antiseptic will be very short. In many cases, to fully remove a biofilm, the composition should be in contact with it for a prolonged period of time, ranging from a few seconds, to several minutes, to an hour or more. The composition may be provided in a gel or cream, which resists immediate evaporation or dispersal. Gels, creams, ointments, oils, and other similar carriers for topical administration are known in the art.

Additionally, for wound treatment, compositions in gel form have the benefit of maintaining moisture at the site of the wound. It is important to keep the wound hydrated during and after treatment with the compositions of the invention. The disclosed compositions are mostly water (generally 95% or more), allowing the wound to remain hydrated while the antiseptic ingredients of the composition fight infection in the wound and prevent new infections from taking hold. Maintaining hydration also prevents the wound from prematurely closing and trapping biofilm inside the tissue. Acetic acid is readily formulated in a gel because acetic acid is not overly reactive. Other organic acids can be used as well, and those that are less reactive are desirable.

Slow-release compositions may be used as well. In some compositions, acetic acid may be encapsulated in lipid soluble nanoparticles, which allow the acetic acid to be carried beneath the surface of a wound before being released from the nanoparticle. Administration with nanoparticles of different properties allows the acetic acid to be released slowly over time, prevent dispersal, and provide other benefits to administration. Acetic acid is freely diffusing, water soluble, and has a high vapor pressure. These properties add to the difficulty of controlling where the acetic acid goes. Nanoparticle encapsulated acetic acid allows the composition to be more precisely controlled. Nanoparticles are described in greater detail below and shown in FIGS. 13 and 14.

In some embodiments, the composition includes some acetic acid that is free from nanoparticles and some acetic acid that is encapsulated within nanoparticles. Alternatively, slow-release formulations may be used on their own or in combination with other instant-acting formulations. For example, a wound may be treated with a composition of acetic acid and hypochlorous acid, and then treated with a composition of mainly acetic acid encapsulated in nanoparticles to provide ongoing release of acetic acid into the deep parts of the wound after the initial treatment.

Production of Hypochlorous Acid Compositions

The basis of compositions and methods of the invention is the protonation of the hypochlorite ion (OCl$^-$). Using HCl or acetic acid (HAc) and NaOCl as an example, the protonation is accomplished by introducing an acid (e.g., HCl) to the solution, which results in the following reaction occurring:

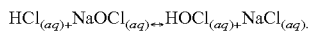

or

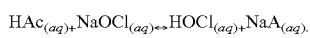

The hypochlorous acid in aqueous solution partially dissociates into the anion hypochlorite (OCl$^-$), thus in aqueous solution there is always an equilibrium between the hypochlorous acid and the anion (OCl$^-$). This equilibrium is pH dependent and at higher pH the anion dominates. In aqueous solution, hypochlorous acid, is also in equilibrium with other chlorine species, in particular chlorine gas, Cl$_2$, and various chlorine oxides. At acidic pH, chlorine gases become increasingly dominant while at neutral pH the different equilibria result in a solution dominated by hypochlorous acid. Thus, it is important to control exposure to air and pH in the production of hypochlorous acid.

Additionally, the concentration of protons (H$_+$) affects the stability of the product. The invention recognizes that the proton concentration can be controlled by using an acid that has a lesser ability at a given pH to donate a proton (i.e., the acid can provide buffering capacity). For example, conducting the process with acetic acid instead of hydrochloric acid is optimal when the desired pH of the final solution is approximately the pKa of acetic acid. This can be achieved by mixing ratios in water of 250× or greater, meaning 1 part proton donor at 100% concentration (e.g., HCl or acetic acid) to 250 parts water.

In certain embodiments, methods of manufacturing HOCl involve mixing together in water in an air-free environment, a compound that generates a proton (H$^+$) in water and a compound that generates a hypochlorite anion (OCl$^-$) in water to thereby produce air-free hypochlorous acid. The water may be tap water or purified water, such as water purchased from a water purification company, such as Millipore (Billerica, Mass.). Generally, the pH of the water is maintained from about 4.5 to about 9 during the method, however the pH may go above and below this range during the production process. Conducting methods of the invention in an air-free environment prevents the build-up of chlorine gases during the production process. Further, conducting methods of the invention in an air-free environment further stabilizes the produced HOCl.

Any compound that produces a hypochlorite anion (OCl$^-$) in water may be used. Exemplary compounds include NaOCl and Ca(OCl)$_2$. In particular embodiments, the compound is NaOCl. Any compound that produces a proton (H$^+$) in water may be used with methods of the invention. Exemplary compounds are acids, such as acetic acid, HCl and H$_2$SO$_4$. In particular embodiments, the compound is HCl. In preferred embodiments, the compound is acetic acid because it is a weaker acid with a preferred pKa to HCl, meaning, it donates fewer protons during the reaction than HCl and is able to maintain the preferred pH level better.

Mixing can be conducted in any type of vessel or chamber or fluidic system. In certain embodiments, a fluidic system 100 as shown in FIG. 1 is used to perform methods of the invention. The system 100 includes a series of interconnected pipes 101a-c with a plurality of mixing devices 102 and 103 in-line with the plurality of pipes 101a-c. The pipes and the mixing devices can be interconnected using seals such that all air can be purged from the system, allowing for methods of the invention to be performed in an air-free environment. In certain embodiments, methods of the invention are also conducted under pressure. Making HOCl in an air-free environment and under pressure allows for the production of HOCl that does not interact with gases in the air (e.g., oxygen) that may destabilize the produced HOCl.

Pipes 101a-c generally have an inner diameter that ranges from about 5 mm to about 50 mm, more preferably from about 17 mm to about 21 mm. In specific embodiments, the pipes 101a-c have an inner diameter of about 21 mm. Pipes 101a-c generally have a length from about 10 cm to about 400 cm, more preferably from about 15 cm to about 350 cm. In certain embodiments, pipes 101a-c have the same length. In other embodiments, pipes 101a-c have different lengths. In specific embodiments, pipe 101a has a length of about 105 cm, pipe 101b has a length of about 40 cm, and pipe 101c has a length of about 200 cm.

The pipes and mixers can be made from any inert material such that material from the pipes and mixers does not become involved with the reaction occurring within the fluidic system. Exemplary materials include PVC-U. Pipes are commercially available from Georg Ficher AB. The pipes and mixers can be configured to have a linear arrangement such that the pipes and the mixers are arranged in a straight line. Alternatively, the pipes and mixers can have a non-linear arrangement, such that the water must flow through bends and curves throughout the process. System 100 shows a non-linear configuration of the pipes 101a-c and mixers 102 and 103.

Pipe 101a is an inlet pipe that receives the water that will flow through the system. Generally, the water in pipes 101a-c is under a pressure of at least about 0.1 bar, such as for example, 0.2 bar or greater, 0.3 bar or greater, 0.4 bar or greater, 0.5 bar or greater, 0.7 bar or greater, 0.9 bar or greater, 1.0 bar or greater, 1.2 bar or greater, 1.3 bar or greater, or 1.5 bar or greater. At such pressures, a turbulent water flow is produced, thus the reagents are introduced to a highly turbulent water flow which facilitates an initial mixing of the reagents with the water prior to further mixing in the mixing devices 102 and 103.

In order to control the pH during the production process, the incoming water should have a buffering capacity in the range of pH 3.5-9.0, more preferably from 6.0 and 8.0, to facilitate addition of the compounds that generates the proton and the compound that generates the hypochlorite anion. The dissolved salts and other molecules found in most tap waters gives the tap water a buffering capacity in the range of pH 5.5-9.0, and thus tap water is a suitable water to be used with methods of the invention.

In certain embodiments, deionized water with the addition of known buffering agents to produce a water having a buffering capacity in the range of pH 3.5-9.0 is used. On example of a buffer in this particular range is phosphate buffer. For greater process control and consistency, using a formulated deionized water may be preferable to using tap water because tap water can change between locations and also over time. Additionally, using deionized water with known additives also ensures a stable pH of the incoming water flow. This process is discussed in greater detail below.

In particular embodiments, an initial pH of the water prior to addition of either the compounds that generates the proton or the compound that generates the hypochlorite anion is at least about 8.0, including 8.1 or greater, 8.2 or greater, 8.3 or greater, 8.4 or greater, 8.5 or greater, 8.6 or greater, 8.7 or greater, 8.8 or greater, 8.9 or greater, 9.0 or greater, 9.5 or greater, 10.0 or greater, 10.5 or greater, or 10.8 or greater. In specific embodiments, the pH of the water prior to addition of either the compound that generates the proton or the compound that generates the hypochlorite anion is 8.4.

Methods of making HOCl include introducing to the water the compound that generates the proton and the compound that generates the hypochlorite anion in any order (e.g., simultaneously or sequentially) and in any manner (aqueous form, solid form, etc.). For example, the compound that generates the proton and the compound that generates the hypochlorite anion are each aqueous solutions and are introduced to the water sequentially, e.g., the compound that generates the proton may be introduced to the water first and the compound that generates the hypochlorite anion may be introduced to the water second.

System 100 is configured for sequential introduction of reagents to the water flow, and the process is described herein in which the compound that generates the proton is introduced to the water first and the compound that generates the hypochlorite anion is introduced to the water second. In certain embodiments, the compound that generates the proton and the compound that generates the hypochlorite anion are introduced to the water in small aliquots, e.g, from about 0.1 mL to about 0.6 mL. The iterative and minute titrations make it possible to control the pH in spite of additions of acid (compound that generates the proton) and alkali (the compound that generates the hypochlorite anion). In certain embodiments, no more than about 0.6 mL amount of compound that generates the proton is introduced to the water at a single point in time. In other embodiments, no more than about 0.6 mL amount of the compound that generates the hypochlorite anion is introduced to the water at a single point in time.

To introduce the reagents to the water, pipe 101a includes an injection port 104 and pipe 101b includes an injection port 105. The injection ports 104 and 105 allow for the introduction of reagents to the water flow. In this embodiments, aqueous compound that generates the proton is introduced to the water in pipe 101a via injection port 104. The compound that generates the proton is introduced by an infusion pump that is sealably connected to port 104. In this manner, the flow rate, and thus the amount, of compound that generates the proton introduced to the water at any given time is controlled. The infusion pump can be controlled automatically or manually. The rate of introduction of the compound that generates the proton to the water is based upon the incoming water quality (conductivity and pH level) and the pressure and the flow of the incoming water. In certain embodiments, the pump is configured to introduce about 6.5 liters per hour of hydrochloric acid into the water. The introducing can be a continuous infusion or in an intermittent manner. Since the water is flowing though the pipes in a turbulent manner, there is an initial mixing of the compound that generates the proton with the water upon introduction of the hydrochloric acid to the water.

Figure 2:
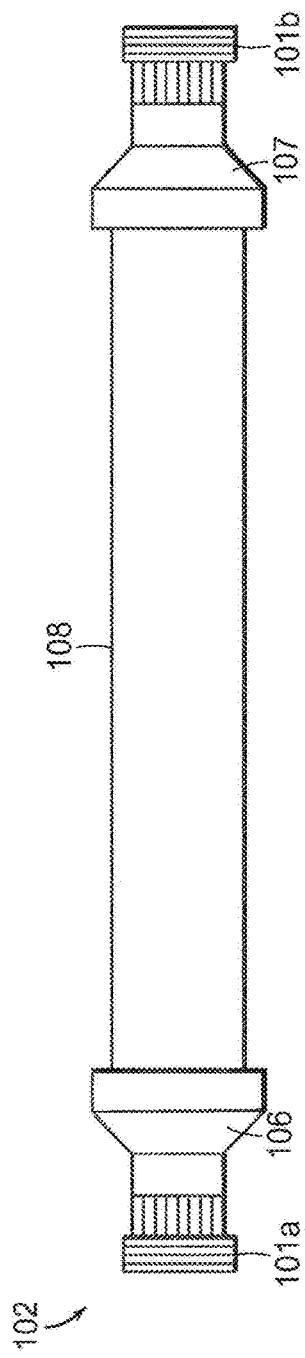
FIG. 2 is a schematic showing a magnified view of the mixing device shown in FIG. 1.

Further mixing occurs when the water enters the first mixing device 102. FIG. 2 shows a magnified view of the mixing device 102 shown in FIG. 1. In the illustrated embodiment, the mixing device includes a length of about 5.5 cm and a diameter of about 5 cm. One of skill in the art will recognize that these are exemplary dimensions and methods of the invention can be conducted with mixing devices having different dimensions than the exemplified dimensions. Mixing device 102 includes a fluidic inlet 106 that sealably couples to pipe 101a and a fluidic outlet 107 that sealably couples to pipe 101b. In this manner, water can enter the mixing chamber 108 of device 102 from pipe 101a and exit the chamber 108 of device 102 through pipe 101b.

Figure 3:
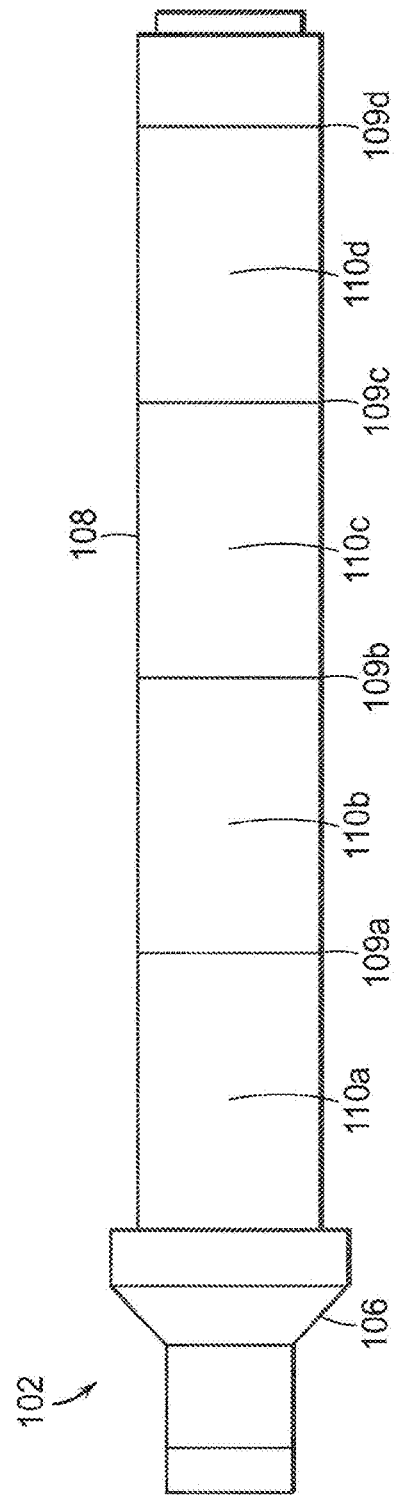
FIG. 3 is a schematic showing an internal view of the mixing chamber of the mixing device.
Figure 4:
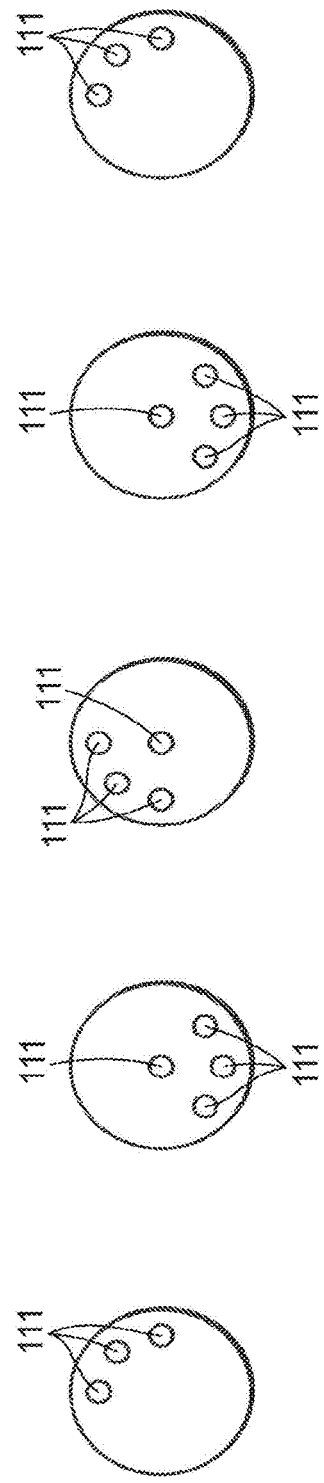
FIG. 4 is a schematic showing a front view of the members that divide the mixing chamber into a plurality of sub-chambers. This view shows the apertures in the members.

The mixing device 102 is configured to produce a plurality of fluidic vortexes within the device. An exemplary device configured in such a manner is shown in FIG. 3, which is a figure providing an internal view of the chamber 108 of device 102. The chamber 108 includes a plurality of members 109, the members being spaced apart and fixed within the chamber 108 perpendicular to the inlet and the outlet in order to form a plurality of sub-chambers 110. Each member 109 includes at least one aperture 111 that allows fluid to flow there through. FIG. 4 shows a front view of the members 109 so that apertures 111 can be seen. The size of the apertures will depend on the flow of water and the pressure in the system.

Any number of members 109 may be fixed in the chamber 108, the number of members 109 fixed in the chamber 108 will depend on the amount of mixing desired. FIG. 4 shows four members 109a-d that are fixed in the chamber to produce four sub-chambers 110a-d. The members 109 may be spaced apart a uniform distance within the chamber 108, producing subchambers 110 of uniform size. Alternatively, the members 109 may be spaced apart at different distances within the chamber 108, producing sub-chambers 110 of different size. The members 109 are of a size such that they may be fixed to an interior wall within the chamber 108. In this manner, water cannot flow around the members and can only pass through the apertures 111 in each member 109 to move through mixing device 102. Generally, the members will have a diameter from about 1 cm to about 10 cm. In specific embodiments, the members have a diameter of about 3.5 cm.

A fluidic vortex is produced within each sub-chamber 110a-d. The vortices result from flow of the water through the apertures 111 in each member 109. Methods of the invention allow for any arrangement of the apertures 111 about each member 109. FIG. 4 illustrates non-limiting examples of different arrangements of the apertures 111 within a member 109. The apertures may be of any shape. FIG. 4 illustrates circular apertures 111. In certain embodiments, all of the apertures 111 are located within the same place of the members 109. In other embodiments, the apertures 111 are located within different places of the members 109. Within a single member 109, all of the apertures 111 may have the same diameter. Alternatively, within a single member 110, at least two of the apertures 111 have different sizes. In other embodiments, all of the apertures 111 within a single member 110 have different sizes.

In certain embodiments, apertures 111 in a member 110 have a first size and apertures 111 in a different member 110 have a different second size. In other embodiments, apertures 111 in at least two different members 110 have the same size. The size of the apertures will depend on the flow of water and the pressure in the system. Exemplary aperture diameters are from about 1 mm to about 1 cm. In specific embodiments, the apertures have a diameter of about 6 mm.

The solution enters mixing device 102 through inlet 106, which is sealably mated with pipe 101a. The solution enters the chamber 108 and turbulent mixing occurs in each of subchambers 110a-d as the solution pass through members 109a-d via the apertures 111 in each member 109a-d. After mixing in the final sub-chamber 110d, the water exits the chamber 108 via the fluidic outlet 107 which is sealably mated to pipe 101b.

The compound that generates the hypochlorite anion is next introduced to the solution that is flowing through pipe 101b via injection port 105. The compound that generates the hypochlorite anion is introduced by an infusion pump that is sealably connected to port 105. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and the flow of the solution. In certain embodiments, the pump is configured to introduce about 6.5 liters per hour of compound that generates the hypochlorite anion into the solution. The introducing can be a continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 103. Mixing device 103 includes all of the features discussed above with respect to mixing device 102. Mixing device 103 may be configured the same or differently than mixing device 102, e.g., same or different number of sub-chambers, same or different diameter of apertures, same or different sizes of sub-chambers, etc. However, like mixing device 102, mixing device 103 is configured to produce a fluidic vortex within each sub-chamber.

The solution enters mixing device 103 through an inlet in the device, which is sealably mated with pipe 101b. The solution enters the mixing chamber and turbulent mixing occurs in each sub-chamber of the mixing device as the solution pass through members in the chamber via the apertures in each member. After mixing in the final sub-chamber, the water exits the chamber via the fluidic outlet in the mixing device which is sealably mated to pipe 101c.

Figure 8:
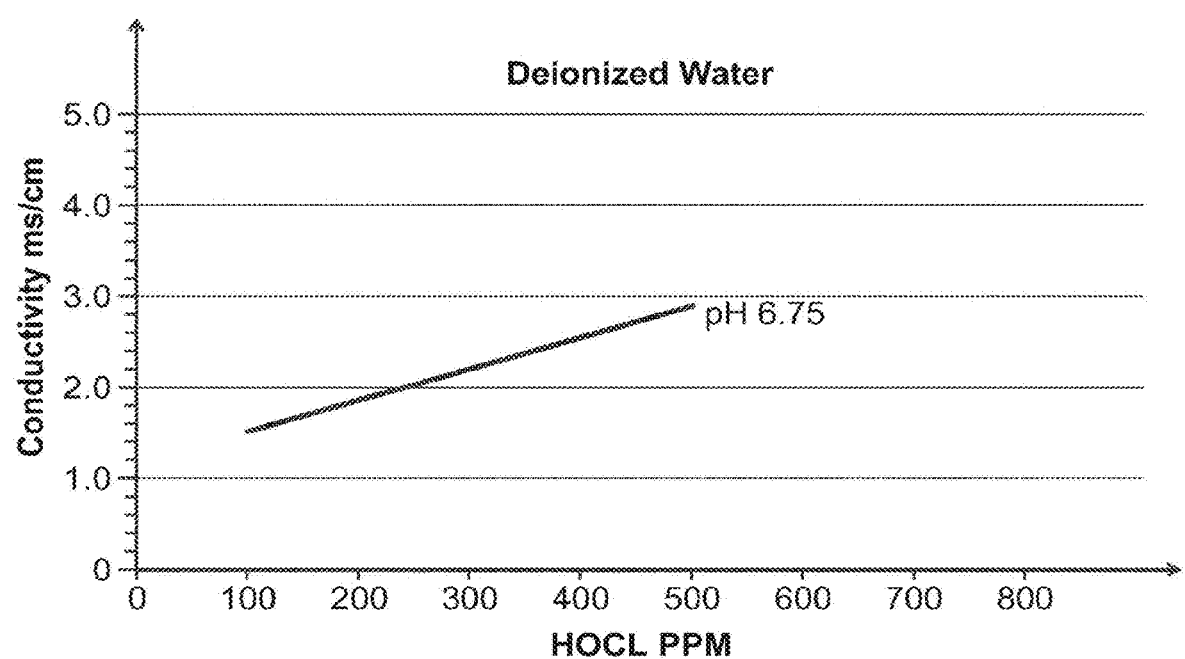
FIG. 8 is a graph of a calibration curve showing HOCl concentration (ppm) calculated indirectly versus conductivity.

At this point, the reaction has been completed and the HOCl has been formed. The production is controlled in-line by measuring pH and conductivity. The pH is used in combination with conductivity based on a pre-calibrated relation between the conductivity and concentration of HOCl measured with spectrophotometry. The measured conductivity is a measure of the solvent's ability to conduct an electric current. Comparing the same matrix with different known concentrations of HOCl and OCl−, a calibration curve (FIG. 8) has been established that is used in combination with the pH meter to regulate the titrations and control the process.

Figure 5:
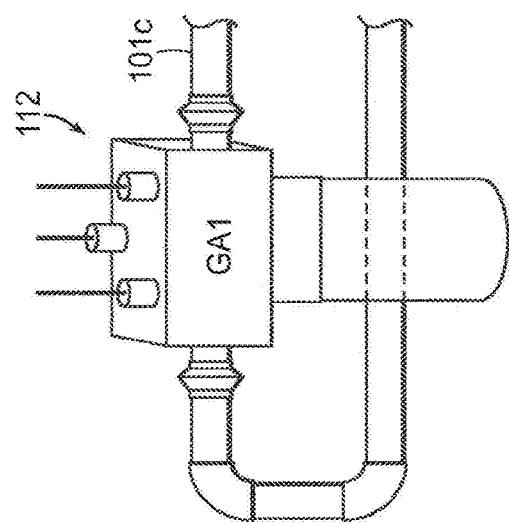
FIG. 5 is a schematic showing a valve configured with measuring sensors for switching from a waste line to a product collection line.
Figure 6:
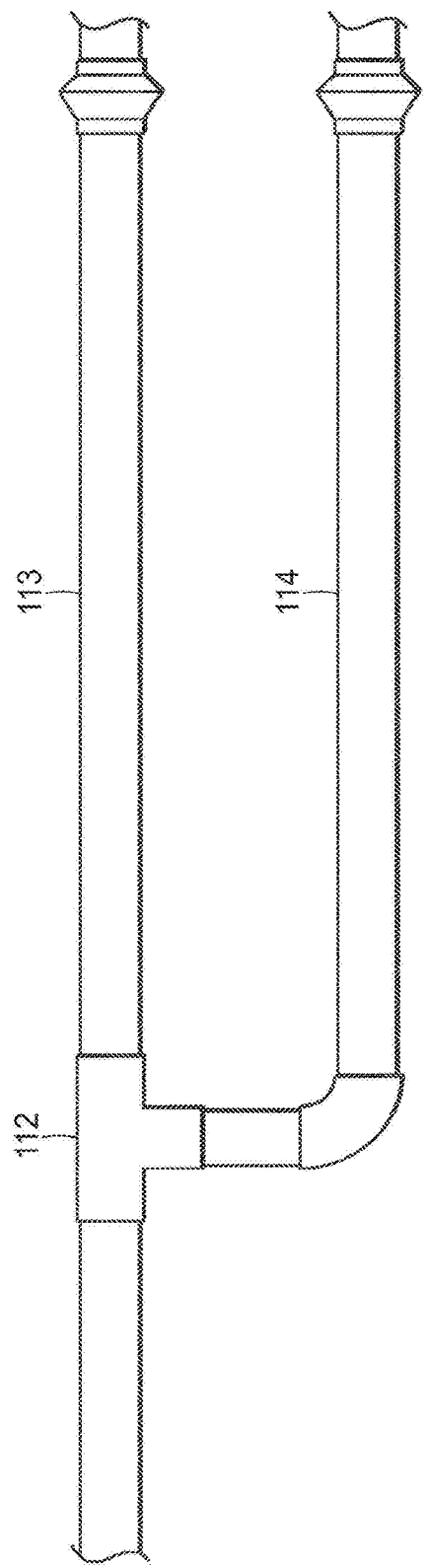
FIG. 6 is a schematic showing the valve in-line with the waste line and the product collection line.

Pipe 101c can be connected to a switch valve 112 that switches between a waste line 113 and a product collection line 114. Shown in FIGS. 5 and 6. The valve 112 includes the pH meter and the conductivity measuring device. These devices measure the concentration (ppm), purity, and pH of the HOCl being produced and provide feedback for altering such properties of the produced HOCl. Once the HOCl being produced in pipe 101c meets the required concentration, purity, and pH, the valve 112 switches from the waste line 113 to the product collection line 114 to collect the desired product.

The HOCl that has been produced in an air-free manner is collected and bottled in an air-free manner. Placing liquids into a bottle in an air-free manner is known in the art. An exemplary method includes placing an inflatable vessel (such as a balloon) into a bottle. The inflatable vessel is connected directly to the collection line 114 and the HOCl is pumped directed into the inflatable vessel in the bottle without ever being exposed to air. Another method involves filling the bottles under vacuum. Another air-free filling method involves filling the bottles in an environment of an inert gas that does not interact with the HOCl, such as an argon environment.

The produced hypochlorous acid is air-free and will have a pH from about 4.5 to about 7.5. However, the pH of the produced HOCl can be adjusted post production process by adding either acid (e.g., HCl) or alkali (e.g., NaOCl) to the produced hypochlorous acid. For example, a pH of between about 4.5 and about 7 is particularly suitable for the application of reprocessing heat sensitive medical instruments. Other applications, such as its use in non-medical environments, for example as in the processing of poultry and fish and general agricultural and petrochemical uses, the breaking down of bacterial biofilm and water treatment, may demand different pH levels.

The process can be performed manually or in an automated manner. Fluidic systems described herein can be operably connected to a computer that controls the production process. The computer may be a PCL-logic controller system. The computer opens and closes the valves for the water inlet, the waste water outlet, and the product outlet according to the feedback received from the sensors in the system (e.g., conductivity, pH, and concentration of product (ppm) being produced). The computer can also store the values for the water pressures and water amounts and can adjust these according to the feedback received from the sensors regarding the properties of the HOCl being produced. The computer can also control the infusion pumps that inject the reagents into the water for the production process.

The process can be performed iteratively in that pipe 101c can be attached to a second fluidic system and the produced HOCl is then flowed through the second system where the process described above is repeated with the starting solution being HOCl instead of water. In this manner, an increased yield of HOCl is produced. Any number of fluidic systems may be interconnected with methods of the invention.

Figure 7:
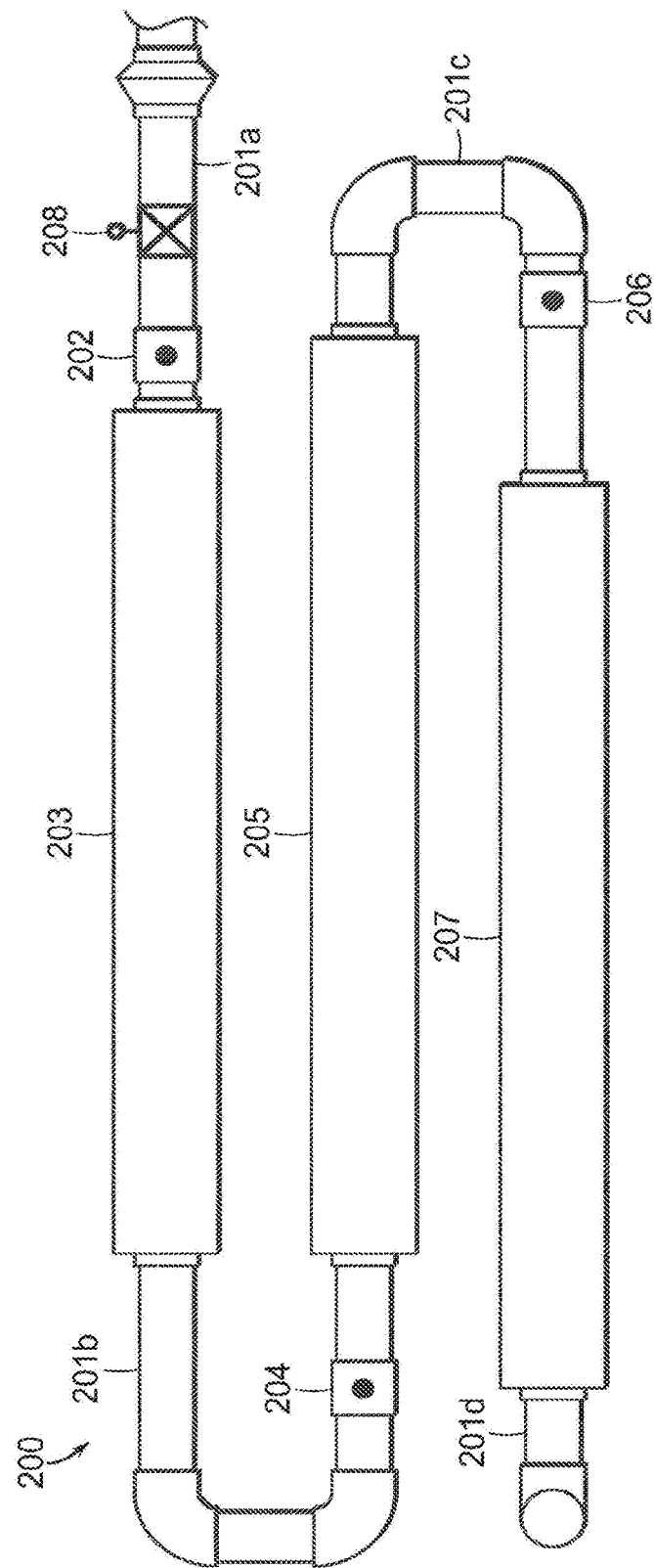
FIG. 7 is a schematic showing another exemplary system for producing hypochlorous acid according to methods of the invention. This system is configured for automated use with buffered deionized water. The buffer can either be included in the inflowing water or can be introduced through an injection port. The buffer may also be mixed during the mixing process by using NaOH in NaOCl or separately injected and acetic acid or others similar acids or bases.

FIG. 7 is a schematic showing another exemplary system 200 for producing hypochlorous acid according to methods of the invention. System 200 is configured for regulation of the pH of the incoming water and injecting buffer for stability. In system 200, water is introduced into pipe 201a. Pipe 201a has a pH meter 208 connected to it. pH meter 208 measures the pH of the incoming water. The pH meter 208 is connected to injection port 202.

The injection port 202 allows for the introduction of at least one buffering agent to the incoming water. The buffering agent is introduced by an infusion pump that is sealably connected to port 202. In this manner, the flow rate, and thus the amount, of buffering agent introduced to the water at any given time is controlled. The infusion pump can be controlled automatically or manually. The rate of introduction of the buffering agent to the water is based upon the incoming water quality (conductivity and pH level), the buffer composition, and the pressure and the flow of the incoming water. The introducing can be a continuous infusion or in an intermittent manner. Since the water is flowing through the pipe 201a in a turbulent manner, there is an initial mixing of the buffering agent with the water upon introduction of the buffering to the water. This initial mixing may be sufficient to properly adjust the properties of the incoming water.

In certain embodiments, further mixing of the water and buffer is performed prior to conducting the process of producing the HOCl. In those embodiments, further mixing occurs when the water with buffering agent enters the first mixing device 203. Mixing device 203 includes all of the features discussed above with respect to mixing device 102. Mixing device 203 may be configured the same or differently than mixing device 102, e.g., same or different number of sub-chambers, same or different diameter of apertures, same or different sizes of subchambers, etc. However, like mixing device 102, mixing device 203 is configured to produce a fluidic vortex within each sub-chamber.

The solution enters mixing device 203 through an inlet in the device, which is sealably mated with pipe 201a. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 202b. The water has a pH of at least about 8.0, preferably 8.4, and a buffering capacity of pH 5.5-9.0.

The process is now conducted as described above for producing HOCl. The compound that generates the proton is next introduced to the water that is flowing through pipe 201b via injection port 204. The compound that generates the proton is introduced by an infusion pump that is sealably connected to port 204. In this manner, the flow rate, and thus the amount, of compound that generates the proton introduced to the water at any given time is controlled. The infusion pump can be controlled automatically or manually. The rate of introduction of the compound that generates the proton to the water is based upon properties of the water (conductivity and pH level), the buffer composition, and the pressure and the flow of the water.

In certain embodiments, the pump is configured to introduce from about 6.5 liters per hour to about 12 liters per hour of compound that generates the proton into the water. The introducing can be a continuous infusion or in an intermittent manner. Since the water is flowing though the pipes in a turbulent manner, there is an initial mixing of the compound that generates the proton with the water upon introduction of the hydrochloric acid to the water.

Further mixing occurs when the solution enters the second mixing device 205. Mixing device 205 includes all of the features discussed above with respect to mixing device 102. Mixing device 205 may be configured the same or differently than mixing device 203, e.g., same or different number of sub-chambers, same or different diameter of apertures, same or different sizes of sub-chambers, etc. However, like mixing device 203, mixing device 205 is configured to produce a fluidic vortex within each sub-chamber.

The solution enters mixing device 205 through an inlet in the device, which is sealably mated with pipe 201b. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 201c.

The compound that generates the hypochlorite anion is next introduced to the solution that is flowing through pipe 201c via injection port 206. The compound that generates the hypochlorite anion is introduced by an infusion pump that is sealably connected to port 206. In this manner, the flow rate, and thus the amount, of compound that generates the hypochlorite anion introduced to the water at any given time is controlled. The infusion pump can be controlled automatically or manually. The rate of introduction of the compound that generates the hypochlorite anion to the water is based upon properties of the solution (conductivity and pH level) and the pressure and the flow of the solution. In certain embodiments, the pump is configured to introduce about 6.5-12 liters per hour of compound that generates the hypochlorite anion into the solution. The amount introduced depends on the desired concentration of HOCl (ppm) and flow of water through the pipes. The introducing can be a continuous infusion or in an intermittent manner. Since the solution is flowing though the pipes in a turbulent manner, there is an initial mixing of the compound that generates the hypochlorite anion with the solution upon introduction of the compound that generates the hypochlorite anion to the solution.

Further mixing occurs when the solution enters the second mixing device 207. Mixing device 207 includes all of the features discussed above with respect to mixing device 102. Mixing device 207 may be configured the same or differently than mixing devices 205 or 203, e.g., same or different number of sub-chambers, same or different diameter of apertures, same or different sizes of sub-chambers, etc. However, like mixing devices 205 and 203, mixing device 207 is configured to produce a fluidic vortex within each sub-chamber.

The solution enters mixing device 207 through an inlet in the device, which is sealably mated with pipe 201c. The solution enters the mixing chamber and turbulent mixing occurs in each sub-chambers of the mixing device as the solution pass through members in the chamber via the apertures in each member. After mixing in the final sub-chamber, the water exits the chamber via the fluidic outlet in the mixing device which is sealably mated to pipe 201d.

At this point, the reaction has been completed and the HOCl has been formed. The produced HOCl can be measured and collected as described above. Pipe 201d can be connected to a switch valve that switches between a waste line and a product collection line. The valve includes a pH meter and a conductivity measuring device. These devices measure the concentration, purity, and pH of the HOCl being produced and provide feedback for altering such properties of the produced HOCl. Once the HOCl being produced in pipe 201d meets the required concentration, purity, and pH, the valve switches from the waste line to the product collection line to collect the desired product.

In another embodiment, a deionizer is placed in-line with incoming water. The deionizer deionizes the water and then a buffering agent is added to the deionized water. The production process is then conducted as described for embodiments of system 200 to produce water having a pH of at least about 8, for example 8.4, and a buffering capacity of pH 6-8.

The HOCl produced by the above process can be used in numerous different applications, for example medical, food-service, food retail, agricultural, wound care, laboratory, hospitality, dental, delignification, or floral industries.

Wound Care

In certain embodiments, compositions of the invention are used for wound care. Wound care involves treating damaged or broken skin, including abrasions, lacerations, ruptures, punctures, or burns. Particular wound care treatments involve treating biofilms. Biofilms may form when free floating microorganisms such as bacteria and fungus attach themselves to a surface. Biofilms are known to impair cutaneous wound healing and reduce topical antibacterial efficiency in healing or treating infected wounds. Other common health conditions related to biofilms include urinary tract infections, middle-ear infections, chronic wounds, and the formation of dental plaque. Cystic fibrosis, native valve endocarditis, otitis media, periodontitis, and chronic prostatitis also involve microorganisms that produce biofilms. Microorganisms commonly associated with biofilms include *Candida albicans*, coagulase-negative staphylococci, *Enterococcus, Klebsiella pneumoniae, Pseudomonas aeruginosa, Staphylococcus aureus*, and others.

Biofilms are often resistant to traditional antimicrobial treatments, and are therefore a serious health risk. The resistance of biofilms renders traditional antibiotic and antimicrobial treatments ineffective. Because biofilms can greatly reduce susceptibility to antibiotics and disinfectants, treatments are needed that are capable of breaking down biofilms but that are not too toxic to the patient.

Methods are provided for administration of a composition to an individual in need of treatment for a biofilm-associated infection. Methods of the invention include prophylaxis, therapy, or cure of a biofilm-associated infection. Methods include administration of one or more unit doses of a composition in a therapeutically or prophylactically effective amount for treatment of an existing biofilm-associated infection or prevention of establishment of a biofilm-associated infection in the individual. In some embodiments, spread of a biofilm-associated infection to another site in the individual is inhibited. In various embodiments, the composition may be administered parenterally, orally, locally, or topically. Compositions may be applied by intravenous, intra-muscular, or subcutaneous injection. In methods of the invention, compositions may be administered in a pharmaceutically acceptable carrier, examples of which are discussed below.

Treatment includes killing of microbes inhabiting the biofilm or removing a biofilm, inhibiting biofilm formation, and disrupting an existing biofilm. The compositions disclosed herein are particularly effective for treatment of microbial biofilms in or on a wound. The composition may be in the form of a topically administrable wound treatment composition which comprises a hypochlorous acid and acetic acid compound. The composition may be combined with an additional antimicrobial agent.

Compositions of the invention can be administered topically to a subject, e.g., by the direct laying on or spreading of the composition on the epidermal or epithelial tissue of the subject. The composition may be formulated as a liquid, powder, lotion, cream, gel, oil, ointment, gel, solid, semi-solid formulation, or aerosol spray. Such formulations may be produced in a conventional manner using appropriate carriers which are well known to a person skilled in the art.

Suitable carriers for topical administration preferably remain in place on the skin as a continuous film, and resist being removed by perspiration or immersion in water. The carrier may include pharmaceutically-acceptable emollients, emulsifiers, thickening agents, solvents, and the like.

The composition may be provided as part of a wound dressing in which the composition is provided within the wound dressing or on the wound-contacting surface thereof. A wound dressing may be intended to be applied to a wound to be treated and which comprises a substrate comprising compositions in accordance with the invention. Such a dressing is particularly convenient because it delivers the composition of the invention to the wound to be treated and simultaneously provides a dressing therefor. The wound dressing may, for example, be fibrous, a foam, a hydrocolloid, a collagen, a film, a sheet hydrogel or a combination thereof. The wound dressing may be in the form of a layered dressing in which one or more layers of the dressing are formed at least in part or one or of; natural fibers, alginate, Chitosan, Chitosan derivatives, cellulose, carboxymethylcellulose, cotton, Rayon, Nylon, acrylic, polyester, polyurethane foam, hydrogels, hydrocolloids, polyvinyl alcohol, starch, a starch film, collagen, hylaronic acid and its derivatives, biodegradable materials, and other materials known in the art. Methods of the invention may further comprise negative-pressure wound therapy, as is known in the art. Such therapies involve applying negative pressure to the wound, such as with a vacuum dressing.

The composition may be administered in a single daily dose or in multiple doses, e.g., 2, 3, 4, or more doses, per day. The total daily amount of composition may be about 0.01 mg, 0.1 mg, 1 mg, 2 mg, etc., up to about 1000 mg. In some embodiments, the total daily amount of administered is about 0.01 mg to about 1 mg, about 1 mg to about 10 mg, about 10 mg to about 100 mg, about 100 mg to about 500 mg, or about 500 mg to about 1000 mg. The actual dosage may vary depending upon the specific composition administered, the mode of administration, the type or location of biofilm to be treated, and other factors known in the art. In some embodiments a dosage can also be selected so as to provide a predetermined amount of composition per kilogram of patient weight.

The use of the compound in conjunction with another known antimicrobial treatment may increase the efficacy of the antimicrobial agent. In some embodiments, methods of the invention further comprise administration (simultaneously or sequentially with compositions of the invention) of one or more doses of an antibiotic substance, including, but not limited to, ciproflaxin, ampicillin, azithromycin, cephalosporin, doxycycline, fusidic acid, gentamycin, linezolid, levofloxacin, norfloxacin, ofloxacin, rifampin, tetracycline, tobramycin, vancomycin, amikacin, deftazidime, cefepime, trimethoprim/sulfamethoxazole, piperacillin/tazobactam, aztreanam, meropenem, colistin, or chloramphenicol. In some embodiments, methods of the invention further comprise administration of one or more doses of an antibiotic substance from an antibiotic class including, but not limited to, aminoglycosides, carbacephem, carbapenems, first generation cephalosporins, second generatin cephalosporins, third generation cephalosporins, fourth generation cephalosporins, glycopeptides, macrolides, monobactam, penicillins, polypeptides, quinolones, sulfonamides, tetracyclines, lincosamides, and oxazolidinones. In some embodiments, methods of the invention comprise administration of a nonantibiotic antimicrobial substance, including but not limited to sertraline, racemic and stereoisomeric forms of thioridazine, benzoyl peroxide, taurolidine, and hexitidine.

Treating Bio Film on Other Tissues

Compositions of the invention can be used to treat biofilms affecting various parts of the body, or attached to various surfaces. In some embodiments, methods of the invention comprise administration of a therapeutically effective composition to an individual in need thereof for treatment of a biofilm-associated infection in the bladder, kidney, heart, middle ear, sinuses, skin, lung, a joint, subcutaneous tissue, soft tissue, vascular tissue, and/or the eye. In other embodiments, a therapeutically effective amount of composition is administered to an individual in need thereof for treatment of one or more of the following conditions associated with biofilm: urinary tract infection; chronic bacterial vaginosis; prostatitis; bacterial infection stemming from diabetes, such as a diabetic skin ulcer; pressure ulcer; venous catheter-associated ulcer; or a surgical wound (e.g., a surgical site infection). In some embodiments, the biofilm is on the skin of an individual. In some embodiments, the biofilm is associated with a wound, including abrasions, lacerations, ruptures, punctures, burns, and chronic wounds. In some embodiments, the biofilm is below the surface of the skin, in subcutaneous tissue, such as a deep tissue wound or a surgical site infection.

Treating Biofilm on Non-Tissue Surfaces

Other applications for treating biofilms are also envisaged. For example, the composition of the invention has application for the treatment of microbial biofilms on surfaces, e.g. surfaces in hospitals (such as operating rooms or patient care rooms) as well as other surfaces (e.g., household work surfaces). The invention also encompasses treating biofilms that form on implanted medical devices and prosthetics.

As is known in the art, implanted medical devices are susceptible to biofilm formation, including fungal biofilms and bacterial biofilms. Methods and compositions of the invention can also be used to treat biofilms that form on the surfaces of implanted medical devices such as catheters and prosthetics. Compositions of the invention can be applied to a medical device pre-implantation. Alternatively, the medical device can comprise a reservoir containing the composition, such that the composition can be released in a controlled manner after implantation. Methods for treating implanted medical devices can be found in U.S. Pat. Nos. 5,902,283 and 6,589,591, and U.S. Patent Publication 2005/0267543, each of which is incorporated by reference herein in its entirety.

Dental Treatment

In another embodiment of the invention, a method is provided for treating an orally-associated biofilm such as dental plaque. The invention provides methods for oral plaque prevention, treating oral plaque infection, treating tooth hypersensitivity, sterilizing a root canal, or treating a dental disease.

Methods of the invention comprise contacting an oral surface, such as teeth, gums, gingiva, or tongue, with a therapeutically effective amount of the composition. Some methods of the invention comprise prevention of an orally-associated biofilm by administration of a prophylactically effective amount of composition to an individual. The composition may be formulated as a dentrifice, such as toothpaste, for treatment or prevention of dental plaque. In other embodiments, the biofilm may be located on the tongue, oral mucosa, or gums. In some embodiments, the composition is formulated as a mouthwash. In some embodiments, the composition is formulated as a paint, foam, gel, or varnish, for example, in a fluoride-containing composition. In an embodiment, the composition is in the form or a gel or foam in a mouthguard that a patient wears for several minutes for fluoride treatment. In other embodiments the composition is contacted to an adhesive strips, which can be applied to the teeth or other oral surface. The composition may comprise a liquid polymer formulation, which is a composition that is preferably topically applied to a surface such as a tooth, to skin, to a mucous membrane, and which dries as a film adhering to that surface, in a manner which resists removal under normal conditions, such as eating or brushing, for applications to the teeth and oral mucosa, or normal washing and abrasion, when applied to skin. Alternatively, the composition may be applied to bandages, dressings, gauze, brushes, implants, etc. and permitted to dry into a film in advance of its administration to a patient.

Mastitis Treatment

In another embodiment of the invention, compositions and methods are provided for treating mastitis. Mastitis is an inflammation tissue in the breast or udder of a mammal. It is often associated with bacterial infections such as *Pseudomonas aeruginosa, Staphylococcus aureus, Staphylococcus epidermidis, Streptococcus agalactiae, Streptococus uberis*, and others. Some of the bacteria known to cause mastitis also form biofilms, but not all mastitis results from biofilm formation.

Mastitis can occur in any mammal, such as humans, cows (dairy cattle), and other animals. Mastitis is a particular problem for dairy cattle. In cattle the condition occurs when leukocytes are released into the mammary gland, often as a response to bacteria in the teat canal. Cows that are repeatedly infected often must be culled to prevent widespread infection in the herd. The loss of milk from infected cows and the loss of cows and entire herds due to infection results in large economic losses for the dairy industry worldwide. In the United States, for example, mastitis is estimated to cost the dairy industry up to $2 billion each year.

Methods are provided for administration of a composition to a mammal in need of treatment for mastitis. Methods of the invention include prophylaxis, therapy, or cure for mastitis. In some embodiments, spread of mastitis to another quarter or to another animal is inhibited.

The formulations, dosages, and routes of administration discussed above are applicable to these embodiments of the invention. For example, in various embodiments, the composition may be administered parenterally, orally, locally, or topically. Compositions may be applied by intravenous, intra-muscular, or subcutaneous injection. Compositions may be applied by infusion via a teat canal, as is known in the art. In methods of the invention, compositions may be administered in a pharmaceutically acceptable carrier, which may include emollients, emulsifiers, thickening agents, solvents, and the like.

The composition may be administered in a single daily dose or in multiple doses, e.g., 2, 3, 4, or more doses, per day. The total daily amount of composition may be about 0.01 mg, 0.1 mg, 1 mg, 2 mg, etc., up to about 1000 mg. In some embodiments, the total daily amount of administered is about 0.01 mg to about 1 mg, about 1 mg to about 10 mg, about 10 mg to about 100 mg, about 100 mg to about 500 mg, or about 500 mg to about 1000 mg. The actual dosage may vary depending upon the specific composition administered, the mode of administration, and other factors known in the art. The composition may be administered in conjunction with another known antimicrobial treatment such as an antibiotic.

Compositions can be administered topically to a cow's udder by directly applying or spreading the composition onto the udder or teat. The composition may be formulated as a liquid, powder, lotion, cream, gel, oil, ointment, gel, solid, semi-solid formulation, or aerosol spray. Methods of the invention may further comprise dipping a teat into the composition. Teat dipping can be used to treat an already infected udder or to prophylactically prevent mastitis from developing. The composition may be applied immediately before milking, immediately after milking, or both. Methods of teat dipping are known in the art, and are described in more detail in U.S. Pat. No. 4,113,854, as well as U.S. Patent Publications 2003/0235560 and 2003/0113384, each of which is incorporated by reference herein in its entirety. Methods may further comprise use of a teat sealant to create a physical barrier for the teat orifice after administration of the composition.

In other embodiments, compositions can be provided via intramammary infusion. Intramammary infusion involves forcing the antibiotic up through the teat canal into the udder. Infusion liquid may comprise a composition disclosed herein in combination with a pharmaceutically acceptable carrier such as canola oil. Prior to infusion, the teat is cleaned, for example with an alcohol swab. An antibiotic infusing device may include a cannula sized and shaped to fit into the teat canal. The cannula may be fully or partially inserted through the streak canal. Methods for infusion are known in the art and are described, for example, in U.S. Pat. Nos. 4,983,634 and 5,797,872, the entirety of each of which is incorporated by reference herein.

Methods of the invention may further comprise administering antibiotics in conjunction with compositions of the invention, or in sequential doses before or after administration of the compositions.

Wounds and Surgical Uses

The compositions can be applied to prevent and treat biofilm on other types of living tissue as well. Tissue includes, for example, skin, mucus membranes, wounds, or ostomies. As has been described above, the composition is useful for wound treatment. Wounds include bedsores, chronic wounds, burns, pressure wounds, diabetes wounds, and other forms of skin trauma. Wounds are often susceptible to biofilm formation, which prevents healing and can lead to chronic conditions. Hypochlorous acid and acetic acid compositions can be used for debridement and cleaning of damaged tissue.

The compositions can also be used in a surgical setting, for treating skin prior to or after an operation. The composition prevents infection that would lead to biofilm formation. At times, an area requiring surgery such as a traumatic wound may already be at risk of having developed a biofilm. The hypochlorous acid composition can be used to disinfect the area prior to surgical incision, which would not only help treat the biofilm but also lessen the likelihood of it spreading to other tissue during surgery. The compositions may be used to disinfect any surface within a surgical operating field.

Other Medical Uses

In addition to wound care, HOCl compositions of the invention can also be used for non-traumatic tissue treatment. They may be used for bladder irrigation, for preventing or treating bladder infections or catheter-associated urinary tract infections, and the like. They may be similarly used to treat infections in the aerodigestive tract such as sinus and lung infections, or infections in the oral cavity, pharynx, paranasal sinuses, sinonasal tract, larynx, pyriform sinus, or esophagus. They can be used to fight microbial growth that leads to infection and to reduce allergens that cause adverse immune responses. The compositions may also be administered to the gastrointestinal tract, including the stomach, intestines, and colon, to combat microbial infections such as gastroenteritis, *Clostridium difficile* infection, and small-intestine bacterial overgrowth (SIBO).

In various other embodiments, the compositions can be administered in the form of eye drops to fight eye infections, or can be used to clean or store contact lenses to prevent bacterial growth and biofilm formation. In other embodiments, the composition can be used as an oral rinse or mouthwash to fight biofilm buildup in the oral cavity, or it can be used to clean or store dentures.

In addition to the use as an antiseptic to treat or prevent biofilms on living tissue, the compositions can be used as a disinfectant on other surfaces such as for use in healthcare facilities, food preparation, cooking utensils, and the like. Compositions can be used to disinfect countertops, hospital beds, or food preparation surfaces.

The compositions can be used to disinfect medical devices and surgical instruments, for example. Medical devices are often initially supplied as sterile, but may require additional or subsequent cleaning and disinfection or sterilization. Reusable medical devices in particular must be sterilized or disinfected prior to reuse. Compositions can be applied to the medical device using any known technique. For example, the composition can be applied by wiping or spreading it onto the surface of the device, by spraying an aerosol or mist form of the composition onto the device, by dipping the device into a vessel containing a volume of the composition, or by placing the device into a flow of the composition such as from a faucet. Additionally or alternatively, medical devices and surgical instruments may also be stored submerged in the composition and removed at the time of use.

Treatment with a hypochlorous acid composition disclosed herein can be done in addition to other known techniques such as autoclaving. Alternatively, the composition can be applied instead of autoclaving. Because heat sterilization is not useful for all devices (e.g., some devices contain delicate parts or electronics that cannot withstand high temperatures), hypochlorous acid compositions are a useful alternative, providing an effective way to sterilize or disinfect such devices.

The compositions can also be used to disinfect implants and prostheses before introducing them to the body. Such devices include orthopedic implants, wires, screws, rods, artificial discs, prosthetic joints, soft tissue fillers, pacemakers, intra-uterine devices, coronary stents, ear tubes, artificial lenses, dental implants, and many others known in the art.

The stabilized hypochlorous acid and acetic acid compositions described herein are useful for both biofilm prevention and biofilm removal on all of the surfaces and tissues discussed herein. Because biofilms make microbes far more resistant to traditional antimicrobial agents, microbes that form biofilms are more able to share and modify their resistance genes and spread into the air and surroundings. As a consequence of biofilm development, a simple infection may become chronic, antibiotics and antiseptics stop working, and new strains of infections emerge.

Both acetic acid (or other organic acids) and hypochlorous acid, however, are particularly useful for treating and preventing biofilms. The HOCl compositions disclosed herein mimic the natural disinfectant of the immune system. Therefore the compositions are not susceptible to microbial resistance. The combination of acetic acid and hypochlorous acid reduce the likelihood of development of antibiotic and antimicrobial resistance because the microbes contained in the biofilm are unable to being treated are unable to The compositions of acetic acid and hypochlorous acid disclosed herein are effective in treating and preventing biofilms, without inducing antimicrobial resistance. Additionally, they are non-toxic, do not sting, and relieve itching.

The various embodiments and uses described above involve a variety of methods of administration, as would be understood in the art.

Hypochlorous acid compositions are particularly effective for transdermal treatment due to the small size of the HOCl molecule. Hypochlorous acid is able to penetrate epithelium and wound surfaces, and so can generally reach deeper tissue layers without requiring injection. This is particularly useful for biofilm infection that forms beneath the top layer of skin. Unlike many other antimicrobial treatments, acetic acid and similar organic acids can penetrate deeper layers of skin without requiring an invasive delivery mechanism.

In some embodiments, however, it may be desirable to prevent the HOCl from penetrating into the skin, and therefore the compositions can be combined with excipients, carriers, emulsifiers, polymers, or other ingredients, examples of which are discussed in U.S. Patent Application 2016/0271171, which is incorporated herein by reference in its entirety.

In addition to topical use, wherein the compositions can be sprayed, wiped, or rubbed onto skin, in other embodiments the compositions may be injected into a particular tissue requiring treatment. The compositions can be ingested in capsule form for administration to the gastrointestinal tract. They can be supplied in slow-release or delayed-release capsules. The compositions can be provided as a suppository for insertion into the rectum or vagina. The compositions can be provided as a spray for release in the vagina. The compositions can be provided as a cloth for wiping male and female genitalia or buttocks.

In other embodiments, the compositions can be provided as a nasal spray for treatment of the aerodigestive tract, which can include treatment of allergic reactions, sinus infections and the like. The nasal spray may be in droplet, aerosol, gel, or powder form. The buffered hypochlorous acid and acetic acid composition can be combined with one or more of a decongestant or an anti-inflammatory or anti-histamine agent, as needed. The composition can be aerosolized with a nasal spray dispenser as is known in the art.

The nasal spray may also include a pharmaceutically acceptable carrier, such as a diluent, to facilitate delivery to the nasal mucosa. The carrier might be an aqueous carrier such as saline. The composition may be isotonic, having the same osmotic pressure as blood and lacrimal fluid. Suitable non-toxic pharmaceutically acceptable carriers are known to those skilled in the art. Various carriers may be particularly suited to different formulations of the composition, for example whether it is to be used as drops or as a spray, a nasal suspension, a nasal ointment, a nasal gel or another nasal form. Other additives, excipients, emulsifiers, dispersing agents, buffering agents, preservatives, wetting agents, consistency aids, and gelling agents may be included as well. Preferably, additives should be chosen that impart the desired characteristic without reducing the stability of the hypochlorous acid. Additives may aid in evenly administering the composition over the mucosa or for reducing or delaying the rate of absorption of the composition.

The composition can be delivered by various devices known in the art for administering drops, droplets, and sprays. The nasal spray composition can be delivered by a dropper, pipet, or dispensing. Fine droplets, sprays, and aerosols can be delivered by an intranasal pump dispenser or squeeze bottle. The composition can also be inhaled via a metered dose inhaler, such as a dry powder inhaler or a nebulizer.

Controlled Release with Nanoparticle Encapsulation

Stable aqueous solutions of hypochlorous acid and/or acetic acid can be encapsulated in nanoparticles that allow controlled release of the acid from the nanoparticles. Controlled release allows persistent anti-microbial protection.

Figure 13:
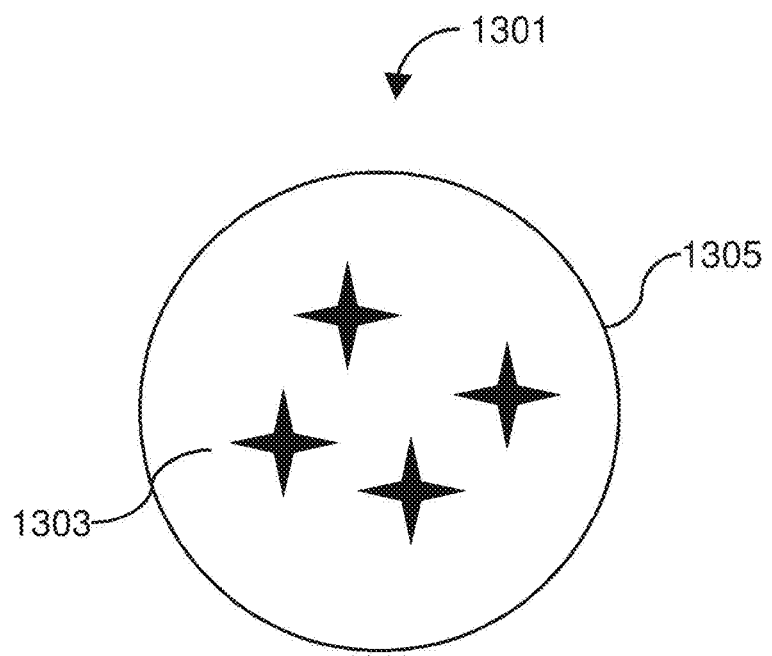
FIG. 13 shows an anti-microbial composition that includes an aqueous solution of hypochlorous acid encapsulated in a nanoparticle.

FIG. 13 shows an anti-microbial composition 1301 comprising an aqueous solution 1303 of hypochlorous acid encapsulated in a nanoparticle 1305. The aqueous solution 1303 of hypochlorous acid is made by a method described herein to produce a solution in which the acid is stable. The stable hypochlorous acid solution 1303 is then encapsulated in nanoparticle 1305. The nanoparticle allows gradual release of the hypochlorous acid. Although not depicted, acetic acid can also be encapsulated in a nanoparticle for controlled release.

The nanoparticle may be any type of nanoparticle that provides controlled release of the acid from the nanoparticle. The nanoparticle may comprise a polymer, such as an organic polymer. Examples of polymers suitable for controlled-release nanoparticles include acrylic acid, carrageenan, cellulosic polymers (e.g., ethyl cellulose or hydroxypropyl cellulose), chitosan, cyclodextrins, gelatin, guar gum, high amylase starch, hyaluronic acid, locust bean gum, pectin, polyacrylamide, poly(D,L-lactide-co-glycolide acid), poly(lactic acid), poly(xylitol adipate salicylate), polyanhydride, poly(ethylene oxide), poly(ethyleneimine), polyglycerol ester of a fatty acid, polysaccharides, polyvinyl alcohol, povidone, sodium alginate, and xanthan gum. For details on the use of polymers to form controlled-release nanoparticles, see Binnebose, et al., *PLOS Negl Trop Dis* 9: e0004713 (2015); Campos, et al., *Scientific Reports* 5:13809 (2015); Dasgupta et al., *Mol. Pharmaceutics* 12:3479-3489; Gao, et al., *The Journal of Antibiotics* 64:625-634, (2011); Lee, et al., *International Journal of Nanomedicine* 11:285-297 (2016); and U.S. Pat. No. 8,449,916 (incorporated by reference). The nanoparticle may contain an aluminosilicate (such as a zeolite, e.g., analcime, chabazite, clinoptilolite, heulandite, leucite, montmorillonite, natrolite, phillipsite, or stilbite), calcium ammonium nitrate, hydroxyapatite (e.g., urea-modified hydroxyapatite), metal hydroxide, metal oxide, polyphosphate, or silicon compound (e.g., silicon dioxide). The nanoparticle may contain lipids, i.e., it may be a lipid nanoparticle. The nanoparticle may include a liposome. For details on the use of liposomes to form controlled-release nanoparticles, see Weiniger et al., *Anaesthesia* 67:906-916 (2012). The liposome may be multi-lamellar. The nanoparticle may contain a gel, sol-gel, emulsion, colloid, or hydrogel. For details on the use of hydrogels to form controlled-release nanoparticles, see Grijalvo et al., *Biomater. Sci.* 4:555 (2016). The nanoparticle may contain a combination of formats, such as a hydrogel encapsulated within a liposome. The nanoparticle may have a coreshell structure. The nanoparticle may be biodegradable. Compositions of the invention may include an anti-metabolic agent.

The anti-metabolic agent may be a metal ion. For example, the anti-metabolic agent may be zinc, copper, or silver.

A nanoparticle that allows controlled release of hypochlorous acid or acetic acid permits diffusion of the acid to occur more slowly than the acid would diffuse from an equal volume of the same aqueous solution of the acid that is not encapsulated in a nanoparticle. The controlled release of hypochlorous acid or acetic acid may be due to permeability characteristics of the nanoparticle, e.g., a nanoparticle that is partially or poorly permeable to the acid. A controlled-release nanoparticle may be a nanoparticle that releases the acid due to degradation of the nanoparticle or impairment of its structural integrity in a time-dependent manner. Release of the acid from the nanoparticle may be triggered by environmental conditions, such as pH, temperature, light, pressure, redox conditions, or the presence of a particular chemical.

Figure 14:
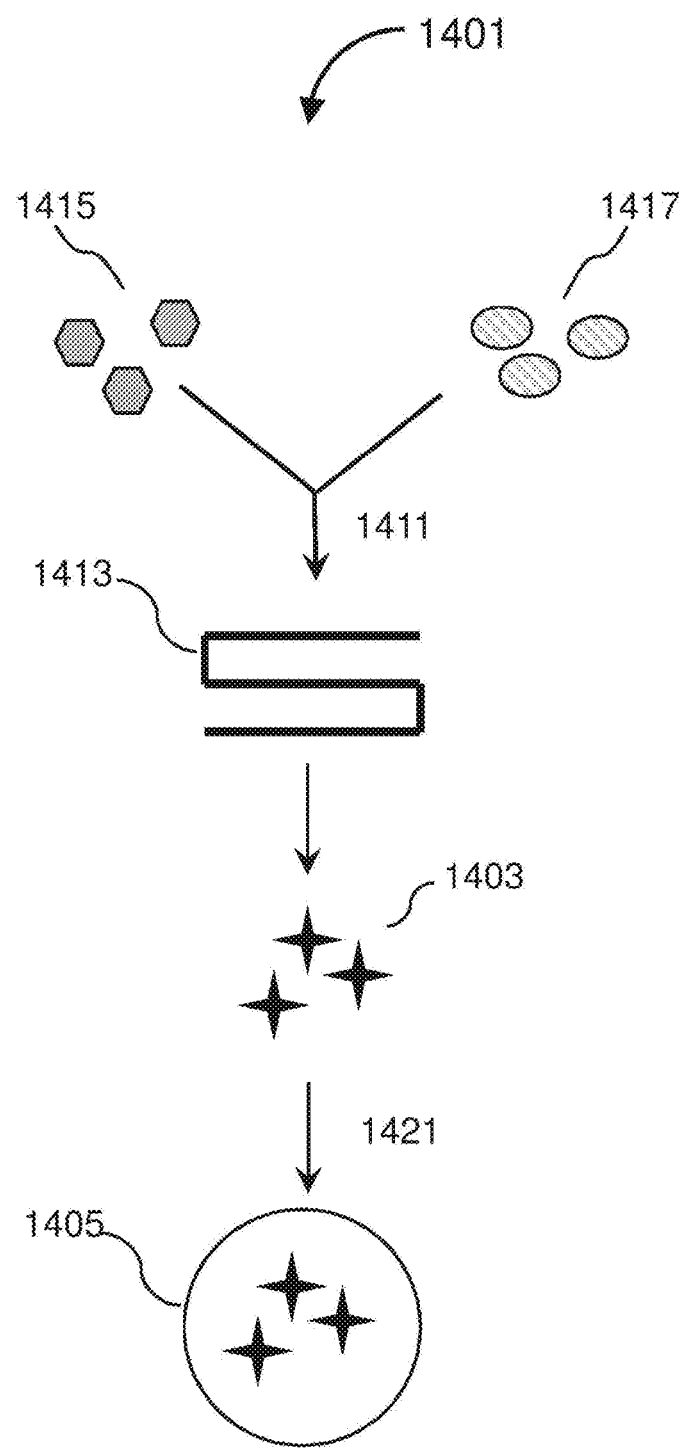
FIG. 14 is an illustration of a method of making an anti-microbial composition that includes an aqueous solution of hypochlorous acid encapsulated in a nanoparticle.

FIG. 14 is an illustration of a method 1401 of making an anti-microbial composition that includes an aqueous solution 1403 of hypochlorous acid encapsulated in a nanoparticle 1405. The method entails mixing 1411 in water in a chamber 1413 from which air has been purged a compound 1415 that generates a proton (H+) in water and a compound 1417 that generates a hypochlorite anion (OCl⁻) in water. The mixing 1411 produces an air-free aqueous solution 1403 of hypochlorous acid. The solution 1403 is then encapsulated 1421 in a nanoparticle 1405. The encapsulation may be performed in an air-free environment to produce a composition that is substantially free of air.

Compositions of Acetic Acid and Hypochlorous Acid for Biofilm Treatment

The disclosed formulations of acetic acid and hypochlorous acid are superior for treating biofilms on surfaces including skin or other tissue. The compositions use a balanced formula where the combination of acetic acid and hypocholorous acid provide greater disinfecting qualities than either substance alone. In fact the present invention recognizes that the particular disclosed combinations provide greater disinfecting power than would be expected by adding the acetic acid and hypochlorous acid. In other words, the compositions have been found to be greater than the sum of their parts. These benefits are shown in the accompanying data in FIGS. 15-21, which demonstrate how the balanced compositions of acetic acid and hypochlorous acid provide enhanced disinfecting capabilities against biofilms and outperform all other products on the market. The differences in performance are shown across a wide range of concentrations.

Additionally, since acetic acid is toxic at high concentrations, the prior art has taught away from its use on skin or other tissue, except in trace amounts. Some of the disclosed compositions contain acetic acid at 2% or greater, and when in combination with HOCl have proven to be safe and effective for treating skin and other tissues. The HOCl in these compositions has been found to have a modulating effect of the acetic acid. This allows the compositions to take advantage of the antimicrobial properties of acetic acid without causing harm to the tissue. Additionally, HOCl has an analgesic function, so it also allows higher concentrations of HAc to be used on skin or other tissue without causing excessive pain or discomfort to the patient.

Figure 15:
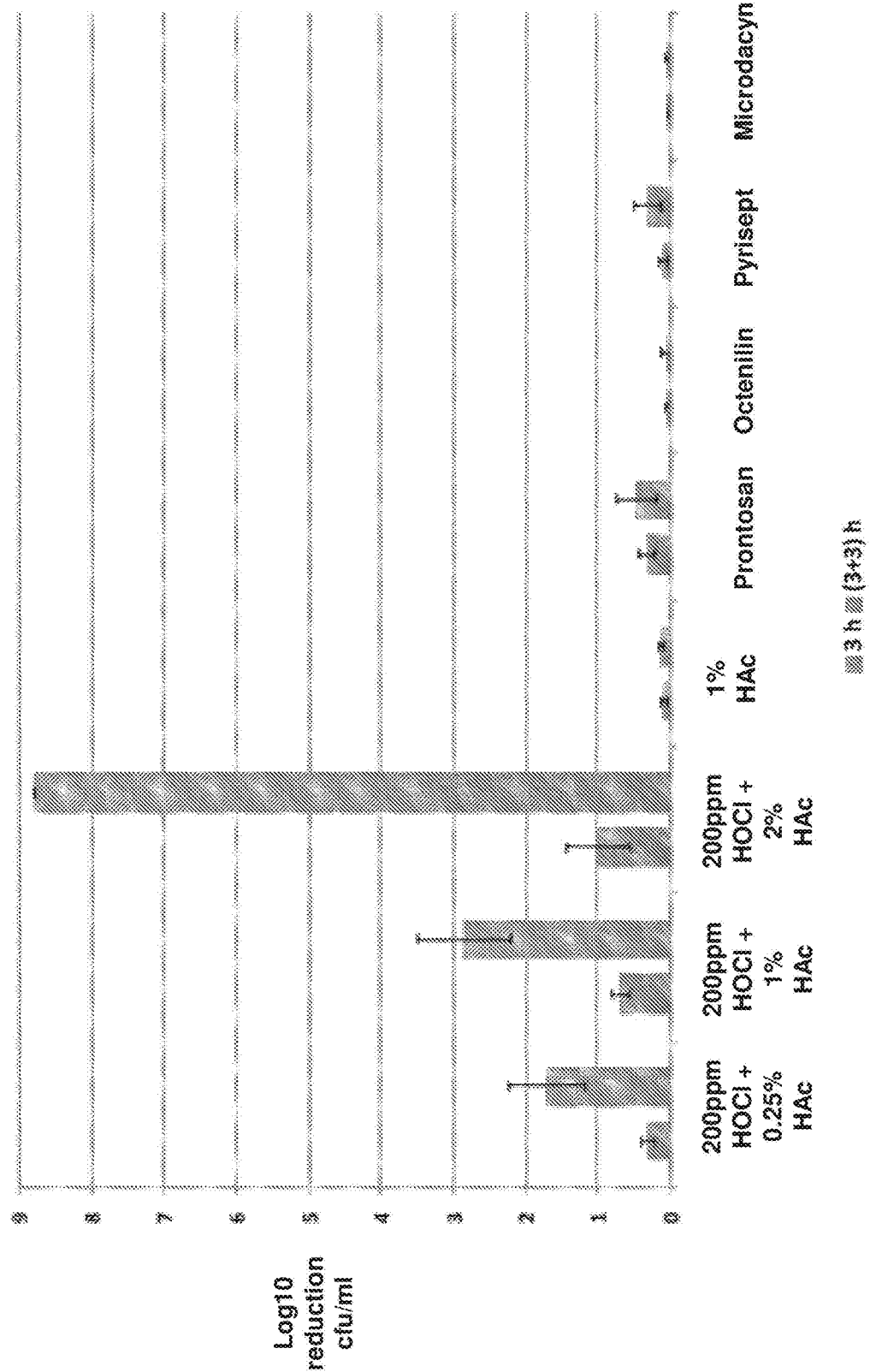

FIG. 15 for example, shows a comparison of various concentrations of HOCl and acetic acid against other commercially available antimicrobial compositions. Eight different treatments were tested, as listed along the x-axis. Each composition was exposed to a 24-hour filter-grown *S. aureus* biofilm, and the reduction in biofilm was measured in colony-forming units per milliliter (cfu/ml) and reported on a log scale along the y-axis. Measurements of the reduction in biofilm were recorded at 3 hours and 6 hours. Each column therefore has two bars, and shows the effect of each composition on the biofilm over time.

The first three columns show the results of 200 ppm HOCl with three different concentrations of acetic acid (0.25%, 1.0%, and 2.0%, respectively). The fourth column shows 1% acetic acid alone. The next four columns show commercially available antimicrobial products: Prontosan; Octenilin; Pyrisept; and Microdacyn, which is a hypochlorous acid composition.

The results show that all three combinations of acetic acid and hypochlorous acid were more effective against the biofilm than any of the other compositions. At 3 hours, test composition A (200 ppm HOCl and 0.25% HAc) performed approximately as well as the Prontosan, the current market leader in biofilm treatment. It also far outperformed the 1% HAc or the other commercially available products. After 6 hours, however, composition A showed much greater efficacy than even Protosan.

Meanwhile, test composition B (200 ppm HOCl and 1.0% HAc) was even more effective at treating biofilm. Comparing composition B with the 1% HAc (in the fourth column) shows the unexpected benefit of the addition of HOCl. Despite having the same concentration of acetic acid, composition B far outperforms the 1% HAc alone at both 3 hours and 6 hours.

Composition C (200 ppm HOCl and 2.0% HAc) showed by far the greatest reduction in biofilm among the tested compositions. At both 3 and 6 hours, it was several orders of magnitude more effective than the commercially available products.

These data show that in addition to being more effective in reducing biofilm than any of the commercially available products, the compositions containing both acetic acid and hypochlorous acid were more effective than acetic acid alone (1% HAc) or hypochlorous acid alone (microdacyn), and those superior results cannot be explained merely by the additive effect of the two components. Without being bound by any particular mechanism, the data show that the acetic acid and hypochlorous acid combination provides a synergistic effect that allows the composition to be more effective than would otherwise be predicted based on the efficacy of each component alone.

Figure 16:
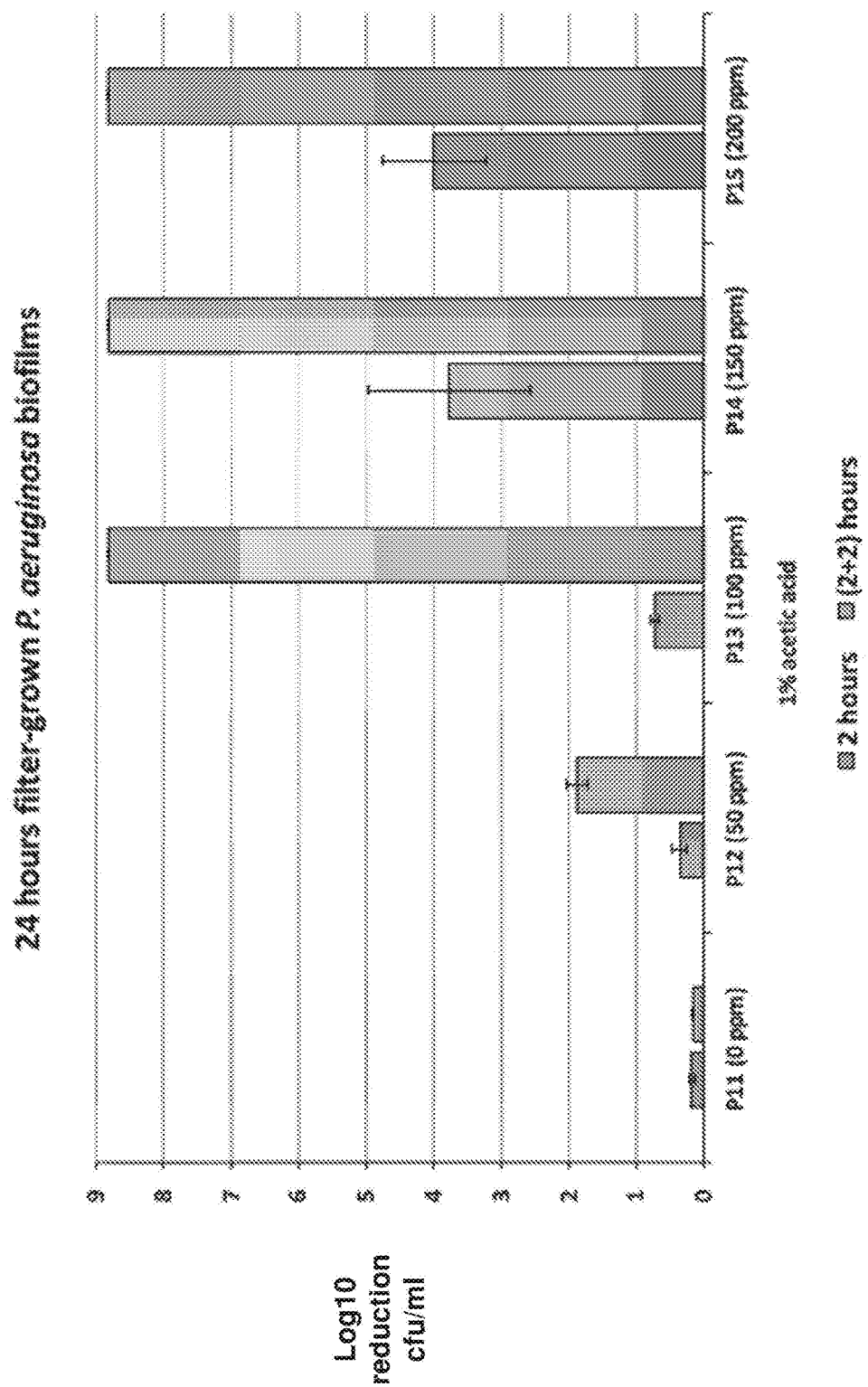

FIGS. 16-19 show the effects of various compositions of HOCl and HAc on *P. aeruginosa* biofilms. FIG. 16 shows a comparison of compositions having 1% acetic acid and varying concentrations of HOCl. Five different treatments were tested with HOCl in concentrations of 0 ppm, 50 ppm, 100 ppm, 150 ppm, and 200 ppm. Each composition was exposed to a 24-hour filter-grown *P. aeruginosa* biofilm, and the reduction in biofilm was measured in colony-forming units per milliliter (cfu/ml) and reported on a log scale along the y-axis. Measurements of the reduction in biofilm were recorded at 2 hours and 4 hours.

As shown in the graph, the reduction at 2 hours was greater with higher concentrations of HOCl, with a particularly significant spike at 150 ppm. At 4 hours, the spike occurs at even lower concentrations of HOCl.

Figure 17:
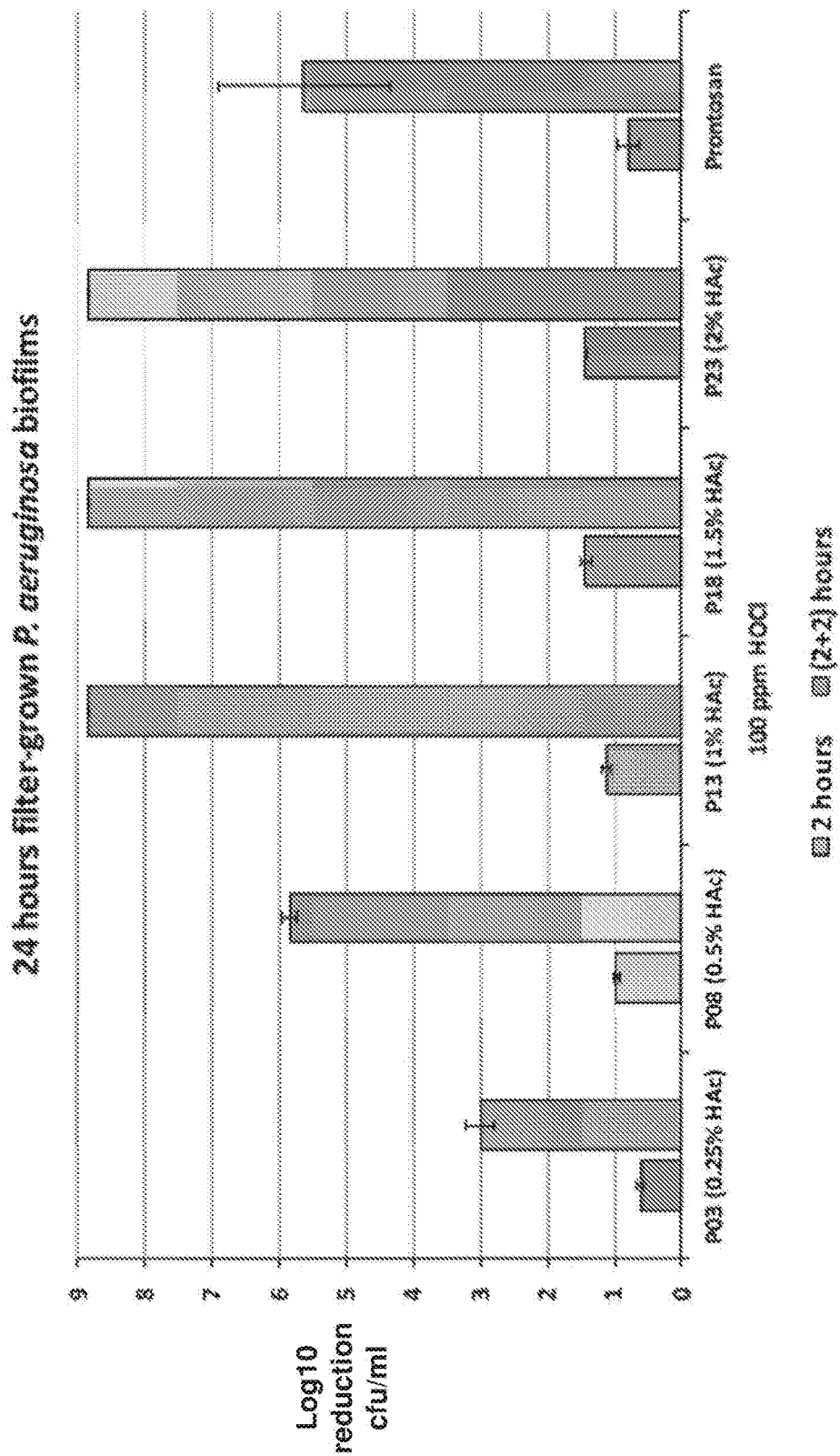

FIG. 17 shows the effects on *P. aeruginosa* of different compositions where the concentration of HOCl is maintained at 100 ppm and the percentage of acetic acid varies from 25% to 2%.

Figure 18:
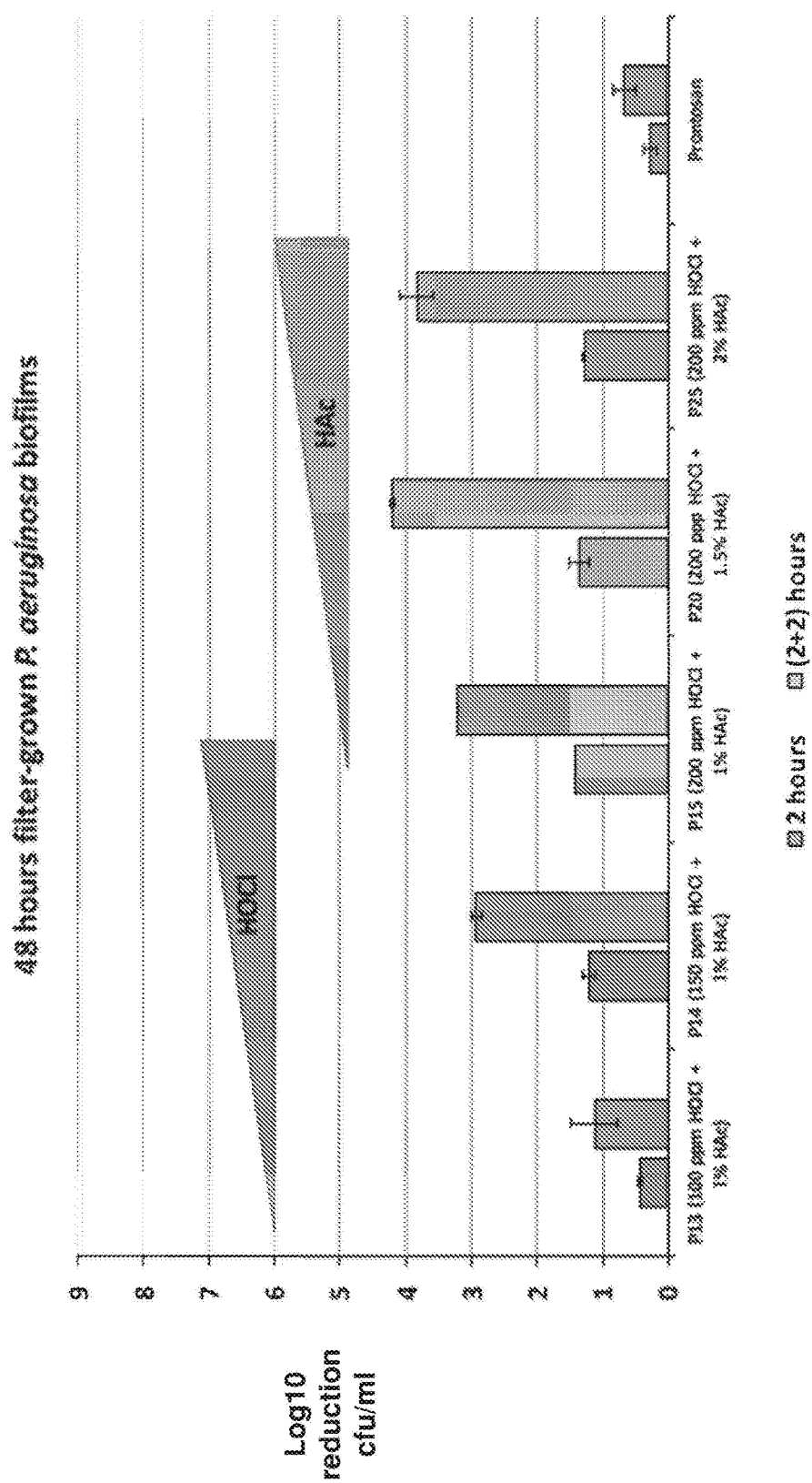

FIG. 18 shows the effects as both HOCl and HAc increase.

Figure 20:
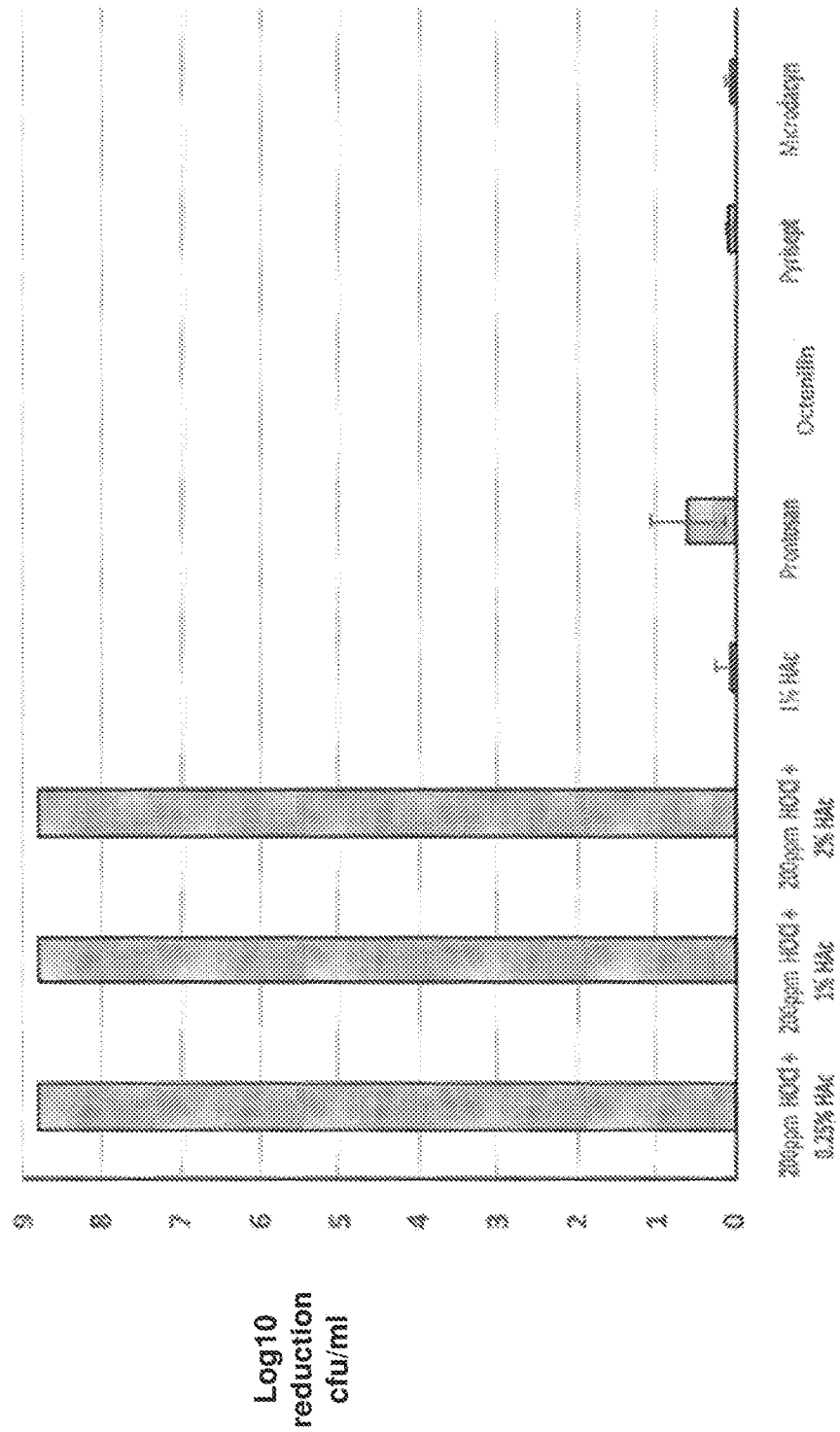
Figure 21:
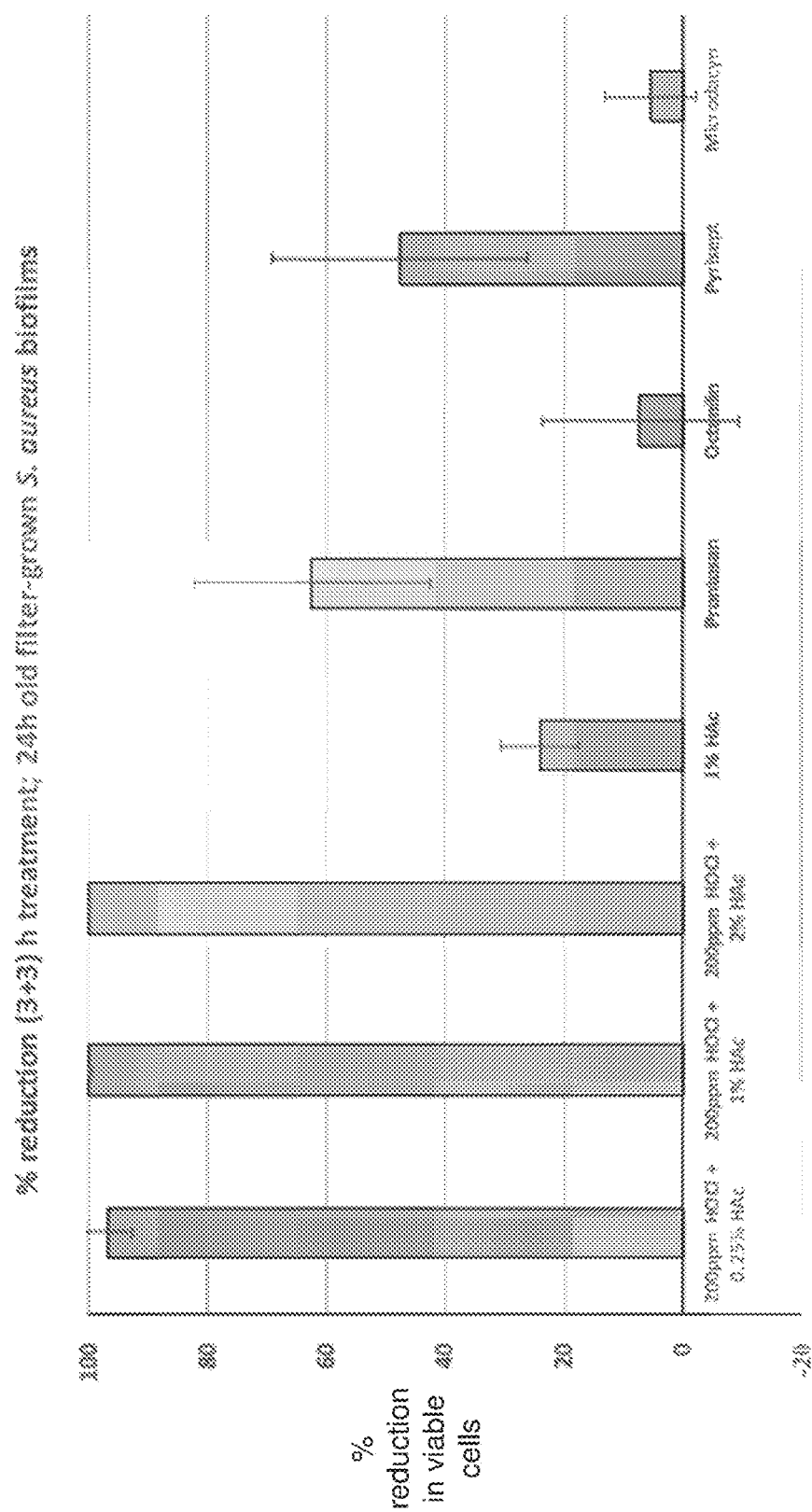

FIGS. 19-21 show different compositions of HOCl and HAc against *S. aureus* and *P. aeruginosa* under various conditions. The figures show the superior results obtained with combinations of hypochlorous acid and acetic acid, which demonstrate the synergistic effect of those two compounds.

The various disclosed formulations may be effective for treating biofilm infections in different types of tissue. For example, the 200 ppm HOCl and 0.25% HAc composition is useful for topical applications such as hand disinfection or mouth wash. This composition is more effective than other commercially available products at treating surface-level biofilms as shown in FIG. 15. For treating penetrating deeper into tissue, or for clearing particularly bad biofilm infections or invasive biofilms that have penetrated beneath the surface, a higher percentage of HAc may be used, such as the formulation of 200 ppm HOCl with 2% HAc. This composition is useful for treating infected wounds, preventing biofilm in wounds, treating eczema, or treating other infections. This formulation has been found to be effective for combating biofilms that have formed in the root of teeth.

FIGS. 20-21 show additional data supporting the unexpected efficacy of acetic acid and hypochlorous acid compositions on various biofilms, particularly as compared to prior art and commercially available compositions. As the figures make clear, various compositions that balance in the concentrations of HOCl and HAc in different ways provide an assortment of disinfecting compositions that can target different types of biofilms on different types of tissue.

Compositions of Hypochlorous Acid and Acetic Acid for Treatment of Transient Bacteria while Maintaining Natural Flora Another benefit of the disclosed HOCl and HAc compositions is that while they are particularly effective at reducing pathogenic biofilms, they have been found not to inhibit growth of "good" or natural biofilms and other microbes that live symbiotically on and in tissue. In fact the present invention recognizes the disclosed compositions are effective for immediately eradicating transient microbes while maintaining levels of natural biofilm.

Tests were performed on the hands of healthy subjects to determine the transient bacteria killing effect of the disclosed compositions. The subjects washed their hands, and dipped their fingertips into *Escherichia coli*. The disclosed compositions were applied to the subjects' hands by rubbing the disclosed compositions into the skin to stimulate the removal of the transient bacteria on the skin. The same test was performed using prior art alcohol compositions. The results provided that the disclosed invention reduced the presence of the transient bacteria by 99.98%, where the prior art compositions reduced the presence of transient bacteria by 99.9%.

In some trials, the good biofilm was reduced at a lesser rate than the pathogenic biofilm, and it grew back faster than the target biofilm did. Specifically, tests were performed on the hands of 20 subjects. The disclosed compositions were applied to the subjects' hands by rubbing the disclosed compositions into the skin to stimulate the removal of the transient bacteria on the skin. In this trial the disclosed compositions were applied multiple times to the hands and forearms of the subjects over 5 minutes to maintain exposure to the disclosed compositions. The same test was performed using prior art alcohol compositions. Bacteria kills were measured immediately after the application and again 3 hours after application. The results provided demonstrated that alcohol has a 99.5% killing effect on the natural biofilm immediately after application and 99.16% effect 3 hours after application. Surprisingly, the disclosed invention had only a 90% killing effect on the natural biofilm immediately after application, and a 99.16% killing effect on the natural biofilm immediately after application.

Surprisingly, the disclosed inventions compared to prior art alcohol-based disinfectants, were more effective at targeting the pathogenic biofilm infection without damaging the good microbes. Therefore, the disclosed compositions are effective at the targeted treatment of biofilm infections, without harming the body's natural flora.

INCORPORATION BY REFERENCE

Any and all references and citations to other documents, such as patents, patent applications, patent publications, journals, books, papers, web contents, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1: Product Analysis

Figure 9:
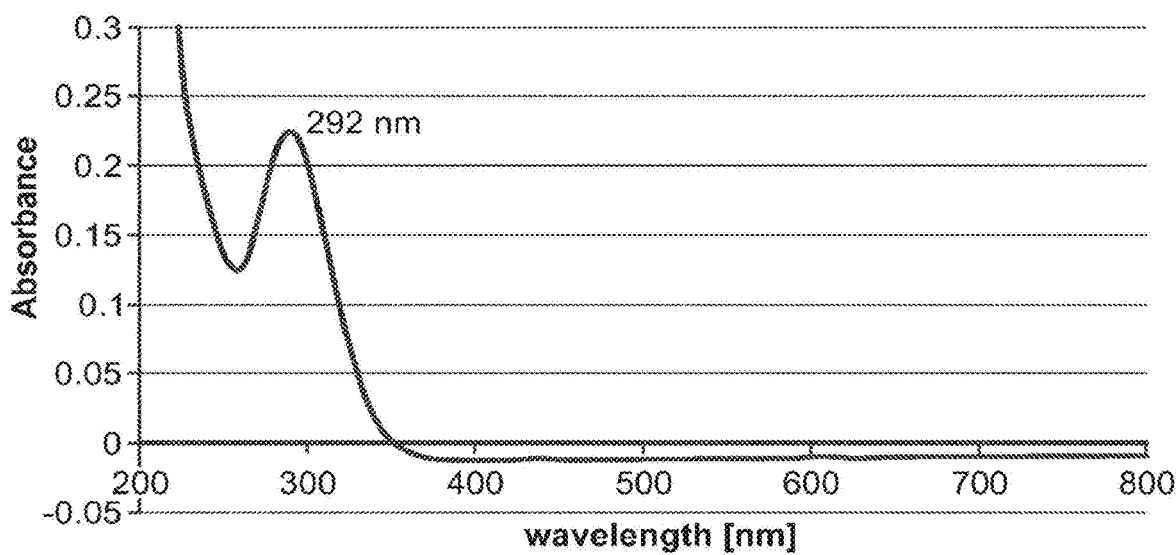
FIG. 9 is a graph showing a spectrophotometric analysis of the produced HOCl. The gases generally produced during production of HOCl are $ClO_2$, $Cl_2O$ and $Cl_2$, all of which are detectable in the visible range as yellow or yellow-red. The graph shows no absorption from colored gases in the produced HOCl.

When spectrophotometry is expanded to also cover the visible range it is possible to detect colors. The gases generally produced during production of HOCl are $ClO_2$, $Cl_2O$ and $Cl_2$, all of which are detectable in the visible range as yellow or yellow-red. Tzanavaras et al. (Central European J. of Chemistry, 2007, 5(1)1-12). Data in FIG. 9 illustrates that the HOCl produced by methods on the invention shows no absorption from colored gases as shown by the lack of colored substance. It is known that HOCl produces a peak at 292 nm (Feng et al. 2007, J. Environ. Eng. Sci. 6, 277-284).

Example 2

HOCl produced by the process described above was stored under heat stress at 40° C. in order to accelerate degradation using four different types of aqueous solutions: (1) reagent grade water (deionized water); (2) tap water; (3) reagent grade water with a phosphate buffer; and (4) tap water with a phosphate buffer. Characteristics of the HOCl product were monitored after the initial reaction (T=0); four weeks (T=4); eight weeks (T=8); and twelve weeks (T=12).

Figure 10:
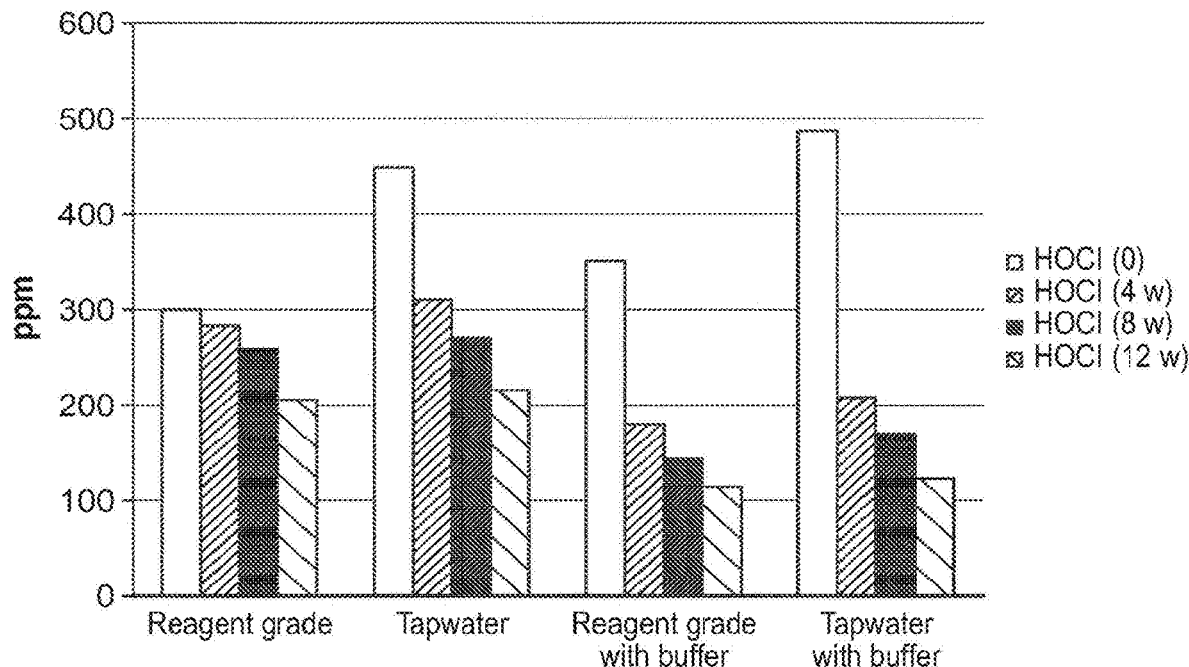
FIG. 10 is a graph showing the amount (parts per million (ppm)) of HOCl initially produced (T=0) and its stability over time.

FIG. 10 is a graph showing the amount (parts per million (ppm)) of HOCl initially produced (T=0) and its stability over time. The data show that the reagent grade water (deionized water) without phosphate buffer is the most stable over the twelve weeks, showing the least amount of product degradation from the initial amount produced. The deionized water produces a much more stable product than that produced using tap water. Additionally, and surprisingly, the data show that phosphate buffer may negatively impact amount of HOCl product produced.

Figure 11:
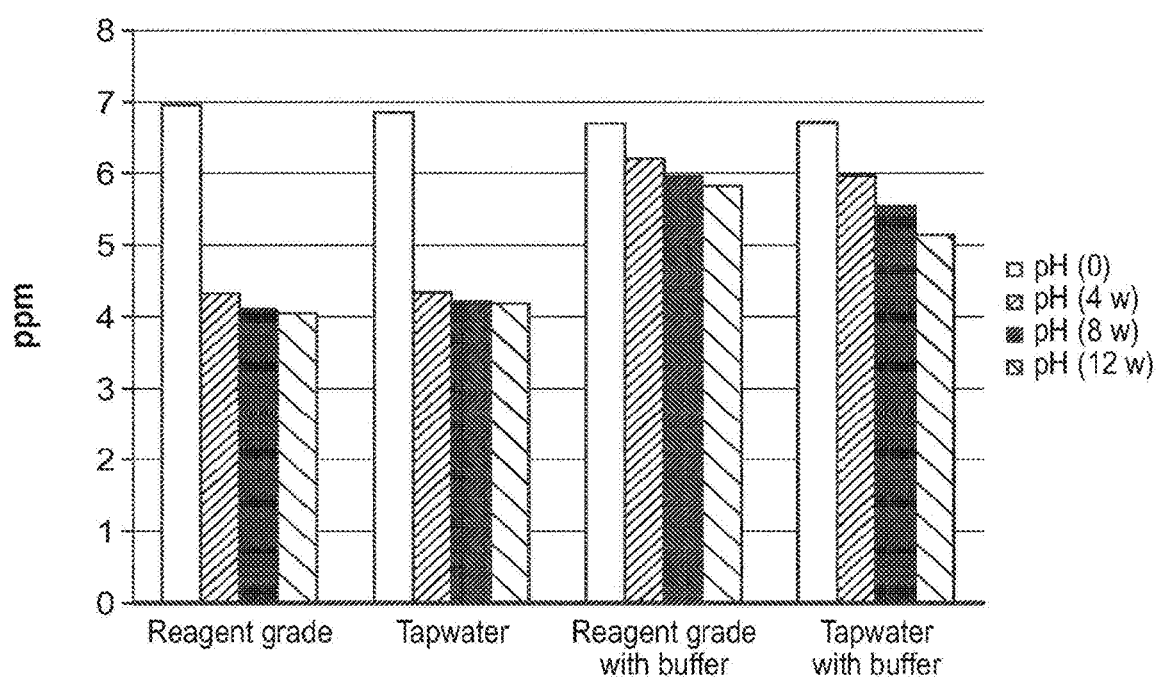
FIG. 11 is a graph showing how the pH of the HOCl product changed over time.

FIG. 11 is a graph showing how the pH of the HOCl product changed over time. In all cases, the pH decreased over time, however, for all cases, the pH stayed in the range of pH=4 to pH=7 over the twelve weeks.

Figure 12:
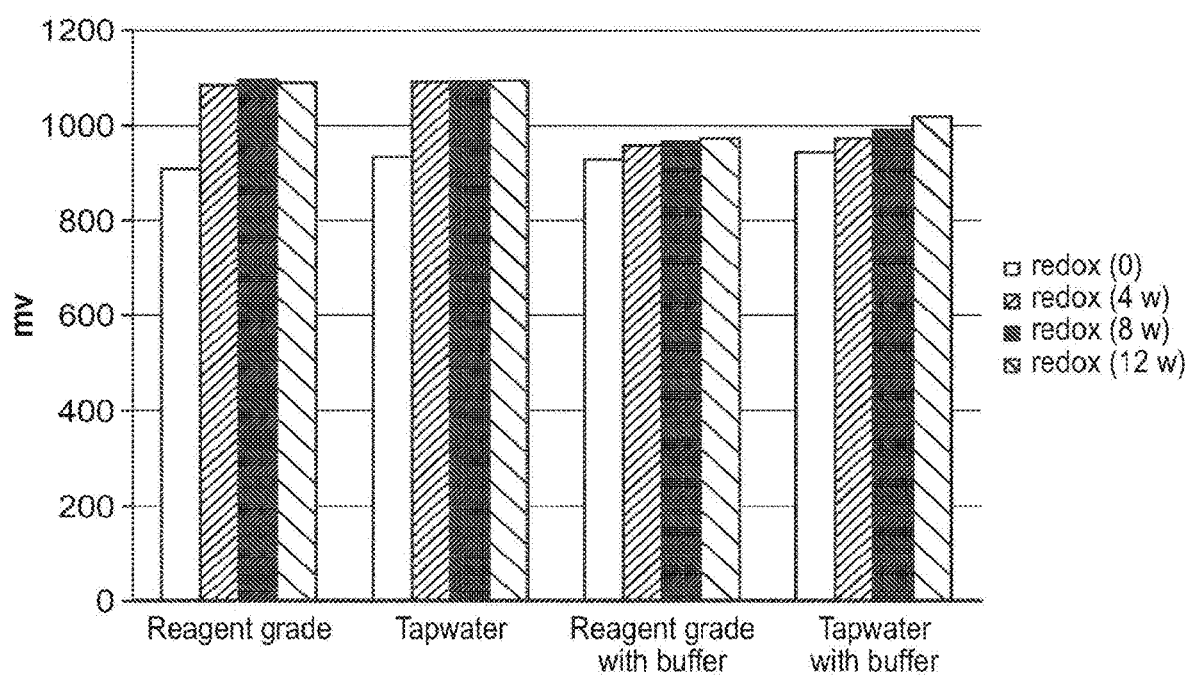
FIG. 12 is a graph showing the oxidation and reduction (redox) of the HOCl product over time.

FIG. 12 is a graph showing the oxidation capacity of the HOCl product over time. The data show that the product retained oxidation capacity over the twelve weeks regardless of the starting water.

Example 3: Acetic Acid Compared to Hydrochloric Acid

Using the above described process, HOCl was produced using hydrochloric acid (HCl) and acetic acid and thereafter stored under heat stress at 40 C. The amount of HOCl initially produced was recorded (T=0) and then the amount of HOCl product remaining after twelve days was recorded. Three batches of each were produced. The data for the HCl produced HOCl is shown in Table 1. The data for the acetic acid produced HOCl is shown in Table 2.

TABLE 1

HOCl produced with HCl

| Batch number | Initial amount (ppm) | Initial pH | Amount after 12 days (ppm) | pH after 12 days | Amount of degradation | Amount pH change |
|---|---|---|---|---|---|---|
| 1 | 192 | 7.12 | 159 | 5.71 | 17.2% | 19.8% |
| 2 | 183 | 5.88 | 147 | 4.01 | 19.7% | 31.8% |
| 3 | 189 | 5.21 | 154 | 3.97 | 18.5% | 23.8% |

TABLE 2

HOCl produced with acetic acid

| Batch number | Initial amount (ppm) | Initial pH | Amount after 12 days (ppm) | pH after 12 days | Amount of degradation | Amount pH change |
|---|---|---|---|---|---|---|
| 1 | 205 | 4.62 | 180 | 4.50 | 12.4% | 2.7% |
| 2 | 205 | 5.33 | 178 | 5.04 | 13.3% | 5.4% |
| 3 | 207 | 4.07 | 178 | 3.89 | 13.9% | 4.6% |

The data show that using acetic acid provides greater product stability, most likely due to greater stability in the pH. Without being limited by any particular theory or mechanism of action, it is believed that the different protonation capacity of acetic acid as compared to hydrochloric acid, i.e., acetic acid donates fewer protons to a liquid than hydrochloric acid, results in greater HOCl stability over time.

Example 4: Hand Disinfectant

Tests were performed on the hands of healthy subjects to determine the transient bacteria killing effect of the disclosed compositions.

In this experiment, 18 subjects washed their hands, and dipped their fingertips into a solution of *Escherichia coli*. Once the subjects' hands were dry, aliquots of the disclosed composition (5 mL of 160 ppm HOCl, 0.13% Hac) were applied to the subjects' dry hands and rubbed into the skin for 30 to stimulate the removal of the transient bacteria on the skin, according to Handrub procedure PN-EN 1500: 2013-07. The same was done using 3 mL of the reference alcohol 2-propanol 60% v/v.

The results provided that both the disclosed composition and the reference alcohol reduced the presence of the transient bacteria by a 4-log reduction.

In another experiment aliquots of the disclosed composition (3 mL of 0.03% HOCl, 0.13% Hac) were applied to each of the hands of 20 subjects. For each of the subjects, one hand was bare and the other had a surgical glove covering it. The composition was rubbed into the hands and forearms for 5 minutes to maintain exposure to the compositions according to Handrub procedure PN-EN 12791:2005. The same was done using 3 mL of the reference alcohol propan-1-ol, 60% v/v for 3 minutes of maintained exposure.

Bacteria kills of *Escherichia coli, Pseudomonas aeruginosa, Staphylococcus areus*, and *Enterococcus hirae* were measured immediately after the application and again 3 hours after application. The results demonstrated that the reference alcohol reduced the natural bacteria by 2.48 logs immediately after application and 2.16-log reduction 3 hours after application. The disclosed composition reduced the natural bacteria by a 0.69 logs 3 hours after application and a 1.01-log reduction immediately after application.

Surprisingly, the disclosed compositions of the present invention compared to the prior art alcohol-based disinfectants, were more effective at targeting transient pathogenic bacteria without damaging the natural bacteria. Therefore, the disclosed compositions are effective at the targeted treatment of pathogenic biofilm infections, without harming the body's natural flora that protects the skin.

What is claimed is:

1. An antimicrobial composition for treating and/or preventing pathogenic bacterial biofilms on a tissue surface without harming natural biofilm of the tissue, the composition comprising a mixture of acetic acid (HAc) and hypochlorous acid (HOCl) having concentrations optimized so as to achieve a synergistic effect resulting in the composition being capable of reducing the presence of transient bacteria on the tissue surface at a greater rate than the presence of natural bacteria on the tissue surface, the HAc having a concentration of 0.13 wt % and the HOCl having a concentration of 0.03 wt %.

2. The composition of claim 1, wherein the tissue is skin tissue.

3. The composition of claim 2, wherein the skin tissue is epidermal tissue.

4. The composition of claim 2, where in the tissue is vaginal tissue.

5. The composition of claim 1, wherein the composition is formulated in a spray, gel, cream, ointment, or oil.

6. The composition of claim 1, wherein the acetic acid is encapsulated in a nanoparticle.

* * * * *